United States Patent
De Porre et al.

(12)

(10) Patent No.: US 6,265,425 B1
(45) Date of Patent: Jul. 24, 2001

(54) COMBINATION OF A RAMBA AND A TOCOPHEROL

(75) Inventors: Peter Marie-Zoë Robert De Porre, Ghent; Jan Paul Jozef Michel Bruynseels, Grobbendonk; Walter Boudewijn Leopold Wouters, Kapellen, all of (BE)

(73) Assignee: Janssen Pharmaceutica, N.V., Beerse (BE)

( * ) Notice: Subject to any disclaimer, the term of this patent is extended or adjusted under 35 U.S.C. 154(b) by 0 days.

(21) Appl. No.: 09/581,891

(22) PCT Filed: Dec. 12, 1998

(86) PCT No.: PCT/EP98/08127

§ 371 Date: Jun. 16, 2000

§ 102(e) Date: Jun. 16, 2000

(87) PCT Pub. No.: WO99/32098

PCT Pub. Date: Jul. 1, 1999

(30) Foreign Application Priority Data

Dec. 19, 1997 (EP) .................................................. 97204019

(51) Int. Cl.[7] ........................ A61K 31/41; A61K 31/415; A61K 31/355

(52) U.S. Cl. ........................... 514/383; 514/396; 514/458

(58) Field of Search ..................................... 514/396, 383, 514/458

(56) References Cited

PUBLICATIONS

Connolly MMet al., "Management of liarozole–associated skin toxicity with alpha tocopherol"; May 1, 1997: Proc Annu Meet Am Soc Clin Oncol; 16: A282.

Dimery I.W. et al., "Phase I trial of alpha–tocopherol effects on 13–cis–retinoic acid toxicity", Jan. 1997; Annals of Oncology pp. 85–89.

*Primary Examiner*—Raymond Henley, III
(74) *Attorney, Agent, or Firm*—Mary Appollina

(57) ABSTRACT

The present invention is concerned with the use of a tocopherol for the manufacture of a medicament for avoiding, alleviating, suppressing or overcoming the adverse side-effects of therapy with a retinoic acid metabolism blocking agent. The present invention is also concerned with the combination of 4-(heteroaryl-methyl)anilines with vitamin E and its use as a medicine.

11 Claims, No Drawings

COMBINATION OF A RAMBA AND A TOCOPHEROL

CROSS REFERENCE TO RELATED APPLICATIONS

This application is a National Stage application under 35 U.S.C. §371 of PCT/EP98/08127 filed Dec. 12, 1998, which claims priority from EP 97.204.019.0, filed Dec. 19, 1997.

The present invention is concerned with the use of a tocopherol, more in particular vitamin E, for the manufacture of a medicament for avoiding, alleviating, suppressing or overcoming the adverse side-effects of therapy with a RAMBA, i.e. a Retinoic Acid Metabolism Blocking Agent, more particularly a 4-(heteroaryl-methyl)aniline compound, especially a N-[4-(heteroaryl-methyl)phenyl]-benzothiazolamine compound. The present invention is also concerned with the combination of 4-(heteroaryl-methyl) anilines with vitamin E and its use as a medicine.

Compounds suppressing the metabolism of retinoids, also denoted as Retinoic Acid Metabolism Blocking Agents (RAMBAs), can be used to control the rate of growth and differentiation of normal, preneoplastic and neoplastic epithelial cells, control the rate of growth and differentiation of normal, preneoplastic and neoplastic cells, whether they are epithelial or mesenchymal; whether they are of ectodermal, endodermal or mesodermal origin, thus making these compounds useful in the treatment of carcinoma and keratinization disorders. They are particularly useful in the treatment of carcinomas, such as, for example, prostate cancer, breast cancer, head- and neck cancer, cervix cancer, skin tumors, lung cancer, esophageal cancer, gastrointestinal cancers, anal cancer, penile cancer, bladder cancer, renal cancer; or keratinization disorders, such as, for example, ichthyosis, psoriasis and severe psoriasis, rosacea, acne, plantar warts, callosities, acanthosis nigricans, lichen planus, molluscum, melasma, corneal epithelial abrasion, geographic tongue, Fox-Fordyce disease, cutaneous metastatic melanoma and keloids, epidermolytic hyperkeratosis, Darier's disease, pityriasis rubra pilaris, congenital ichthyosiform erythroderma, hyperkeratosis palmaris et plantaris, melasma, hyperpigmentation and premalignant lesions, such as, for example, Morbus Bowden, pin (prostate intraepithelial neoplasia), cin (cervical intraepithelial neoplasia), leukoplakia.

EP-0,371,559 discloses the use of (1H-imidazol-1-yl) methyl-1H-benzimidazoles as RAMBAs, i.e. they suppress the metabolism of retinoids. Amongst the compounds mentioned therein, 5-[3-chlorophenyl]-1H-imidazol-1-ylmethyl]-1H-benzimidazole has been tested clinically and is known as liarozole.

Vitamin E , α-tocopherol, is a phenol that is widespread in plant materials. It appears to have several functions in animals, but one important function seems to be as a radical scavenger. Vitamin E has the following structure:

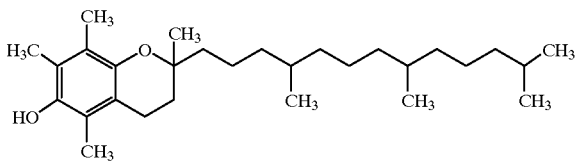

The chemical systematic name of vitamin E is 3,4-dihydro-2,5,7,8-tetramethyl-2-(4,8,12-trimethyltridecyl)-2H-1-benzopyran-6-ol. In literature, vitamin E may refer to various alpha-tocopherol derivatives, stereoisomers and mixtures thereof. Vitamin E is commercially available as various alpha-tocopherol derivatives, stereoisomers and mixtures thereof and also as e.g. the acetate or the succinate.

Other interesting tocopherols are beta-tocopherol, i.e. 3,4-dihydro-2,7,8-trimethyl-2-(4,8,12-trimethyltridecyl)-2H-1-benzopyran-6-ol; gamma-tocopherol, i.e. 3,4-dihydro-2,5,7,8-tetramethyl-2-(4,8,12-trimethyltridecyl)-2H-1-benzopyran-6-ol; delta-tocopherol, i.e. 3,4-dihydro-2,8-dimethyl-2-(4,8,12-trimethyltridecyl)-2H-1-benzo-pyran-6-ol; epsilon-tocopherol, 3,4-dihydro-2,5,8-trimethyl-2-(4,8,12-trimethyl-3,7,11-tridecatrienyl)-2H-1-benzopyran-6-ol; zeta-1-tocopherol, i.e. 3,4-dihydro-2,5,7,8-tetramethyl-2-(4,8,12-trimethyl-3,7,11-tridecatrienyl)-2H-1-benzopyran-6-ol; zeta-2-tocopherol, i.e. 3,4-dihydro-2,5,7-trimethyl-2-(4,8,12-trimethyltridecyl)-2H-1-benzopyran-6-ol; eta-tocopherol, i.e. 3,4-dihydro-2,7-dimethyl-2-(4,8,12-trimethyltridecyl)-2H-1-benzopyran-6-ol.

For the purpose of this invention actually also a prodrug of a tocopherol and in particular of vitamin E will do.

The term "prodrug" refers to a product that releases a tocopherol or, in particular, vitamin E once administered to the patient. The term "prodrug" may refer to another compound wherein there is a covalent bond between the tocopherol and the rest of the compound, said covalent bond being a bond which is easily broken once administered to the patient. Examples of such bonds which are easily broken are ester bonds or amide bonds. The term "prodrug" may also refer to inclusion complexes or other types of complexes which release a tocopherol, in particular, vitamin E once it is administered to the body.

Aside from relieving symptoms of its deficiency in animals, vitamin E displays no notable pharmacological effects or toxicity. Numerous contradictory findings and claims for the actions and mechanisms of action characterize the literature on vitamin E. In acting as an antioxidant, vitamin E presumably prevents oxidation of essential cellular constituents, such as ubiquinone (coenzyme Q), or prevents the formation of toxic oxidation products , such as peroxidation products from unsaturated fatty acids that have been detected in its absence. Diets high in polyunsaturated fatty acids increase an animal's requirement for vitamin E. However, other chemically unrelated substances, such as synthetic antioxidants, selenium, some sulfur-containing amino acids, and the coenzyme Q group, are able to prevent or reverse some of the symptoms of vitamin E deficiency in animal species. In animals vitamin E also affords protection against various drugs, metals and chemicals that can initiate free-radical formation. However, no such protection has been observed in man. Some symptoms of vitamin E deficiency in animals are not relieved by other antioxidants, and it is presumed in these cases that the vitamin is acting in a more specific way.

There is an apparent relationship between vitamin A and E. The intestinal absorption of vitamin A is enhanced by vitamin E, and hepatic and other cellular concentrations of vitamin A are elevated; this may be related to its protection by the antioxidant properties of vitamin E. In addition, vitamin E seems to protect against various effects of hypervitaminosis A. (*Goodman and Gilman, The Pharmacological Basis of Therapeutics,* seventh edition, page 1587).

Vitamin E is commercially available, for instance, in nutritional supplements often in the form of a cocktail of several vitamins and other ingredients.

It is known that liarozole, as a prominent member of the retinoic acid metabolism blocking agents (RAMBAs), has some particular side-effects, such as nausea, vomiting or fatigue. Furthermore patients taking liarozole show symptoms of skin or mucosa linked toxicities, such as, for example, dry skin, peeling skin, flaking skin, pruritus, dry lips, cheilitis, dry mouth. However, liarozole does not show several toxicities seen with hypervitaminosis A or administration of exogenous retinoids such as influence on lipid metabolism, retinoic acid syndrome or visus disturbances.

Unexpectedly, it has been found that administering a tocopherol, in particular, vitamin E or a prodrug thereof ameliorates the retinoic acid metabolism blocking agent (RAMBA) related adverse effects.

The present invention encompasses the combination of a tocopherol, in particular vitamin E, or a prodrug thereof and a retinoic acid metabolism blocking agent (RAMBA).

The present invention encompasses the combination of a tocopherol, in particular, vitamin E and a retinoic acid metabolism blocking agent (RAMBA), more in particular, 4-(heteroaryl-methyl)anilines of formula (I) and (II), the N-oxides, the pharmaceutically acceptable addition salts and the stereochemically isomeric forms thereof, said 4-(heteroaryl-methyl)anilines having the formula

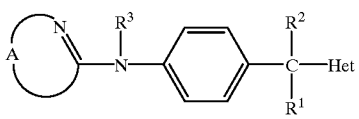
(I)

wherein:
$R^1$ represents hydrogen, hydroxy, $C_{1-6}$alkyl or aryl;
$R^2$ represents hydrogen; $C_{1-12}$alkyl; $C_{3-7}$cycloalkyl; $C_{2-8}$alkenyl; aryl; pyrrolidinyl optionally substituted with $C_{1-4}$algyl or $C_{1-4}$alkyloxycarbonyl; or $C_{1-12}$alkyl substituted with one or two substituents selected from $C_{3-7}$cycloalkyl, hydroxy, $C_{1-4}$alkyloxy, cyano, amino, mono- and di($C_{1-4}$alkyl)amino, mono- and di(aryl)-amino, aryl$C_{1-4}$alkylamino, ($C_{1-4}$alkyl)(aryl$C_{1-4}$alkyl) amino, pyrrolidinyl, piperidinyl, piperazinyl optionally substituted with $C_{1-4}$alkyl, morpholinyl, perhydro-azepinyl, carboxyl, $C_{1-4}$alkyloxycarbonyl, aminocarbonyl, mono- and di($C_{1-4}$alkyl)aminocarbonyl, aryl, aryloxy and arylthio;
$R^3$ represents hydrogen, $C_{1-6}$alkyl, aryl or $C_{1-6}$alkyl substituted with aryl;
Het represents an unsaturated heterocycle selected from imidazolyl, triazolyl, tetrazolyl and pyridinyl; each of said unsaturated heterocycles may optionally be substituted with amino, mercapto, $C_{1-6}$alkyl, $C_{1-6}$alkylthio or aryl;

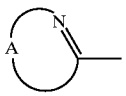

represents an unsaturated mono- or bicyclic heterocycle selected from the group consisting of pyridinyl, pyridazinyl, pyrimidinyl, pyrazinyl, quinolinyl, isoquinolinyl, purinyl, phtalazinyl, cinnolinyl, quinazolinyl and quinoxalinyl; each of said unsaturated mono- or bicyclic heterocycles may optionally be substituted with one, two or three substituents selected from hydroxy, halo, nitro, amino, $C_{1-6}$alkyl, hydroxy$C_{1-6}$alkyl, polyhalo$C_{1-6}$alkyl, $C_{1-6}$alkyloxy, $C_{1-6}$alkylthio, formyl, carboxyl, mono- or di($C_{1-6}$alkyl)amino, $C_{1-6}$alkyloxycarbonyl or aryl; or

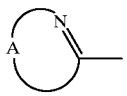

represents a radical of formula

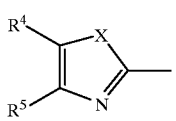
(a)

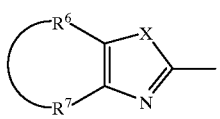
(b)

wherein:
each X independently represents $NR^8$, O, S, S(=O) or $S(=O)_2$; wherein $R^8$ is hydrogen, $C_{1-6}$alkyl, aryl or aryli$C_{1-6}$alkyl;
$R^4$ and $R^5$ each independently represent hydrogen, hydroxy, halo, cyano, nitro, amino, $C_{1-6}$alkyl, hydroxy$C_{1-6}$alkyl, polyhalo$C_{1-6}$alkyl, $C_{1-6}$alkyloxy, formyl, carboxyl, mono- or di($C_{1-6}$alkyl)amino, $C_{1-6}$alkyloxycarbonyl or aryl;
—$R^6$—$R^7$— represents a bivalent radical of formula:

| | |
|---|---|
| —$CR^9$=$CR^9$—$CR^9$=$CR^9$— | (b-1); |
| —N=$CR^9$—$CR^9$=$CR^9$— | (b-2); |
| —$CR^9$=N—$CR^9$=$CR^9$— | (b-3); |
| —$CR^9$=$CR^9$—N=CR9— | (b-4); |
| —$CR^9$=$CR^9$—$CR^9$=N— | (b-5); |
| —$CR^9$=N—N=$CR^9$— | (b-6); |
| —$CR^9$=N—$CR^9$=N— | (b-7); |
| —$CR^9$—$CR^9$—N=N— | (b-8); |
| —N=N—$CR^9$=$CR^9$— | (b-9); |
| —N=$CR^9$—N=$CR^9$— | (b-10); |
| —N=$CR^9$—$CR^9$=N— | (b-11); |
| —$CR^9$=N—N=N— | (b-12); |
| —N=$CR^9$—N=N— | (b-13); |
| —N=N—$CR^9$=N— | (b-14) | or

| | |
|---|---|
| —N=N—N=$CR^9$— | (b-15); | wherein each $R^9$ independently represents hydrogen, hydroxy, halo, nitro, amino, $C_{1-6}$alkyl, hydroxy$C_{1-6}$alkyl, polyhalo$C_{1-6}$alkyl, $C_{1-6}$alkyloxy, formyl, carboxyl, mono- or di($C_{1-6}$alkyl)amino, $C_{1-6}$alkyloxycarbonyl or aryl; and
aryl represents phenyl or phenyl substituted with one, two or three substituents selected from hydroxy, halo, cyano, amino, mono- or di($C_{1-6}$alkyl)amino, $C_{1-6}$alkyl, polyhalo$C_{1-6}$alkyl, hydroxy$C_{1-6}$alkyl, $C_{1-6}$alkyloxy, formyl, carboxyl and $C_{1-6}$aLkylcarbonyl; or two adjacent carbon atoms on said phenyl may be substituted by a single bivalent radical having the formula $C_{1-12}$alkanediyl or polyhalo$C_{1-12}$alkanediyl; and

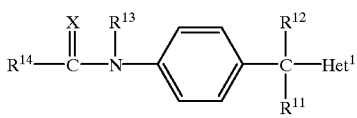
(II)

wherein:

X represents O, S or $NR^{13}$;

$R^{11}$ represents hydrogen, hydroxy, $C_{1-6}$alkyl or $aryl^1$;

$R^{12}$ represents hydrogen; $C_{1-12}$alkyl; $C_{3-7}$cycloalkyl; $C_{2-8}$alkenyl; $aryl^1$; $Het^2$; or $C_{1-12}$alkyl substituted with one or two substituents selected from $C_{3-7}$cycloalkyl, hydroxy, $C_{1-4}$alkyloxy, cyano, amino, mono- and di($C_{1-4}$alkyl)amino, mono- or di($aryl^1C_{1-4}$alkyl)aamino, di($aryl^1C_{1-4}$alkyl)aminocarbonyloxy, ($C_{1-4}$alkyl)($aryl^1C_{1-4}$alkyl)amino, mono- and di(aryl)amino, ($C_{1-4}$alkyl)(di($C_{1-4}$alkyl)-amino$C_{1-4}$alkyl)amino, pyrrolidinyl, piperidinyl, piperazinyl optionally substituted with $C_{1-4}$alkyl, morpholinyl, perhydro-azepinyl, carboxyl, $C_{1-4}$alkyloxycarbonyl, aminocarbonyl, mono- and di($C_{1-4}$alkyl)aminocarbonyl, $aryl^1$, $aryl^1$oxy and $aryl^1$thio; or $R^{11}$ and $R^{12}$ taken together may form a bivalent radical of formula $—R^{11}—R^{12}—$ wherein $—R^{11}—R^{12}—$ represents $—(CH_2)_n—$ wherein n is 2, 3, 4, 5 or 6;

$R_{13}$ represents hydrogen, $C_{1-6}$akyl, $aryl^1$, $Het^2$ or $C_{1-6}$alkyl substituted with $aryl^1$ or $Het^2$;

$R^{14}$ represents hydrogen; hydroxy; mercapto; $C_{1-6}$alkyloxy; $C_{1-6}$alkylthio; $aryl^1$oxy; $aryl_1$thio; $Het^2$-oxy; $Het^2$-thio; $C_{1-12}$alkyl optionally substituted with one, two or three substituents each independently selected from halo, hydroxy, mercapto, $C_{1-6}$alkyloxy, $C_{1-6}$alkylthio, $aryl^1$oxy, $aryl^1$thio, $Het^2$-oxy, $Het^2$-thio, $C_{37}$cycloalkyl optionally substituted with hydroxycarbonyl$C_{1-6}$alkyl, carboxyl, $C_{1-6}$alkyloxy-carbonyl, $aryl^1C_{1-6}$alkyloxy, $aryl^1C_{1-6}$alkylthio, $aryl^1$, $Het^2$; $C_{2-8}$alkenyl optionally substituted with one, two or three substituents selected from halo, $C_{3-7}$cycloalkyl, $aryl^1$, $Het^2$; $C_{2-8}$alkynyl optionally substituted with halo, $C_{3-7}$cycloalkyl, $aryl^1$; $C_{3-7}$cycloalkyl optionally substituted with $C_{1-6}$alkyl or $aryl^1$; $C_{5-7}$cycloalkenyl optionally substituted with $C_{1-6}$alkyl or $aryl^1$; $aryl^1$; $Het^2$; or

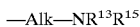  (i)

or

  (ii)

wherein Alk represents $C_{1-6}$alkanediyl; and $R^{15}$ represents hydrogen, $C_{1-6}$alkyl, $aryl^1$, $Het^2$, ($aryl^1$ or $Het^2$)$C_{1-6}$alkyl, ($aryl^1$ or $Het^2$)carbonyl or ($aryl^1$ or $Het^2$)$C_{1-6}$alkyloxycarbonyl;

$aryl^1$ represents indanyl, indenyl, naphtyl, 5,6,7,8-tetrahydro-2-naphtalenyl, phenyl; said indanyl, indenyl, naphtyl or phenyl may be substituted with one, two, three, four or five substituents each independently selected from hydroxy, halo, nitro, cyano, amino, azido, mono- or di($C_{1-6}$alkyl)amino, $C_{1-6}$alkylcarbonylamino, $C_{1-6}$alkyl, polyhalo$C_{1-6}$alkyl, hydroxy$C_{1-6}$alkyl, phenyl, phenyloxy, phenyl$C_{1-6}$alkyloxy, pyridinyl$C_{1-6}$alkyloxy, $C_{1-6}$alkyloxy, formyl, carboxyl and $C_{1-6}$alkylcarbonyl; or two adjacent carbon atoms on said phenyl may be substituted by a single bivalent radical having the formula $C_{1-12}$alkanediyl or polyhalo$C_{1-12}$alkanediyl;

$Het^1$ represents an unsaturated heterocycle selected from pyrrolyl, pyrazolyl, imidazolyl, triazolyl, tetrazolyl and pyridinyl; each of said unsaturated heterocycles may optionally be substituted with amino, mercapto, $C_{1-6}$alkyl, $C_{1-6}$alkylthio or aryl; and $Het^2$ represents a monocyclic heterocycle selected from pyrrolidinyl, pyrrolyl, pyrazolyl, imidazolyl, 1,3,4-triazolyl, 1,2,4-triazolyl, tetrahydrofuranyl, furanyl, thiolanyl, thienyl, dioxolanyl, isoxazolyl, oxazolyl, isothiazolyl, thiazolyl, isoxazolidinyl, oxazolidinyl, isothiazolidinyl, thiazolidinyl, piperidinyl, pyridinyl, piperazinyl, pyridazinyl, pyrimidinyl, pyrazinyl, 1,2,3-triazinyl, 1,2,4-triazinyl, tetrahydropyranyl, pyranyl, morpholinyl and dioxanyl; each of said monocyclic heterocycles may be optionally substituted with one or two substituents each independently selected from $C_{1-4}$alkyl, hydroxy, amino, halo, aryl, arylcarbonyl or $C_{1-4}$alkyloxycarbonyl; or a bicyclic heterocycle selected from indolinyl, indolyl, indazolyl, benzimidazolyl, benzotriazolyl, benzofuranyl, benzothienyl, 2H-1-benzopyranyl, 3,4-dihydro-2H-1-benzopyranyl, benzthiazolyl, isoquinolinyl, quinolinyl, 3,4-dihydroquinolinyl, cinnolinyl, quinazolinyl, quinoxalinyl, chromanyl, 1,4-benzodioxinyl, 1,4-benzoxathianyl, benzodioxanyl and benzodioxolanyl; each of said bicyclic heterocycles may be substituted with one or two substituents each independently selected from $C_{1-4}$alkyl, hydroxy, amino, halo, aryl, arylcarbonyl or $C_{1-4}$alkyloxycarbonyl.

As used in the foregoing definitions and hereinafter, halo is generic to fluoro, chloro, bromo and iodo; $C_{3-7}$cycloalkyl is generic to cyclopropyl, cyclobutyl, cyclopentyl, cyclohexyl and cycloheptyl; $C_{2-8}$alkenyl defines straight and branch chained hydro-carbon radicals containing one double bond and having from 2 to 8 carbon atoms such as, for example, ethenyl, 1-propenyl, 2-butenyl, 2-pentenyl, 3-pentenyl, 3-methyl-2-butenyl, 3-hexenyl, 3-heptenyl, 2-octenyl and the like; $C_{1-4}$alkyl defines straight and branched chain saturated hydrocarbon radicals having from 1 to 4 carbon atoms such as, for example, methyl, ethyl, propyl, butyl, 1-methylethyl, 2-methylpropyl, 2,2-dimethylethyl and the like; $C_{1-6}$alkyl is meant to include $C_{1-4}$alkyl and the higher homologues thereof having 5 or 6 carbon atoms such as, for example, pentyl, 2-methylbutyl, hexyl, 2-methylpentyl and the like; $C_{1-12}$alkyl is meant to include $C_{1-6}$alkyl and the higher homologues thereof having from 7 to 12 carbon atoms such as, for example, heptyl, octyl, nonyl, decyl, undecyl, dodecyl, 2-methylhexyl, 3-ethyloctyl and the like; $C_{1-2}$alkanediyl defines bivalent straight and branched chain saturated hydrocarbon radicals having from 1 to 12 carbon atoms such as, for example, 1,1-methanediyl, 1,2-ethanediyl, 1,3-propanediyl, 1,4-butanediyl, 1,5-pentanediyl, 1,6-hexanediyl, 1,2-propanediyl, 2,3-butanediyl, 1,7-heptanediyl, 1,8-octanediyl, 1,9-nonanediyl, 1,10-decanediyl, 1,11-undecanediyl, 1,12-dodecanediyl, 1,1,4,4-tetramethylbutane-1,4-diyl and the like; polyhalo$C_{1-6}$alkyl is defined as polyhalosubstituted $C_{1-6}$alkyl, in particular $C_{1-6}$alkyl substituted with 1 to 6 halogen atoms, more in particular difluoro- or trifluoromethyl; polyhalo$C_{1-12}$alkanediyl is defined as polyhalo-substituted $C_{1-12}$alkanediyl, in particular $C_{1-12}$alkanediyl substituted with 1 to 12 halogen atoms; triazolyl is meant to include 1,2,4-triazolyl and 1,3,4-triazolyl; tetrazolyl is meant to include 1H-tetrazolyl and 2H-tetrazolyl.

The unsaturated heteroaryl groups represented by Het, Het$^1$ and Het$^2$ may be attached to the remainder of the molecule of formula (I) or (II) through any ring carbon or heteroatom as appropriate. Thus, for example, when the heteroaryl group is imidazolyl, it may be a 1-imidazolyl, 2-imidazolyl, 4-imidazolyl and 5-imidazolyl; when it is triazolyl, it may be 1,2,4-triazol-1-yl, 1,2,4-triazol-3-yl, 1,2,4-triazol-5-yl, 1,3,4-triazol-1-yl and 1,3,4-triazol-2-yl.

The pharmaceutically acceptable addition salts as mentioned hereinabove are meant to comprise the therapeutically active non-toxic base and acid addition salt forms which the compounds of formula (I) and (II) are able to form. The acid addition salt form of a compound of formula (I) and (II) that occurs in its free form as a base can be obtained by treating said free base form with an appropriate acid such as an inorganic acid, for example, hydrohalic acid, e.g. hydrochloric or hydrobromic, sulfuric, nitric, phosphoric and the like acids; or an organic acid, such as, for example, acetic, hydroxyacetic, propanoic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The compounds of formula (I) and (II) containing acidic protons may be converted into their therapeutically active non-toxic base, i.e. metal or amine, addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

Conversely said salt forms can be converted by treatment with an appropriate base or acid into the free acid or base form.

The term addition salt as used hereinabove also comprises the solvates which the compounds of formula (I) and (II) are able to form and said solvates are meant to be included within the scope of the present invention. Examples of such solvates are, e.g. the hydrates, alcoholates and the like.

The compounds of formula (I) wherein R$^1$ and R$^2$ are different and the compounds of formula (II) wherein R$^{11}$ and R$^{12}$ are different have at least one asymmetric carbon atom in their structure, the absolute configuration of which may be represented by the descriptors R and S. Formulas (I) and (II) are intended to encompass all enantiomers and diastereoisomers of the compounds of the invention as well as the mixtures thereof, in particular the racemates and the enantiomerically pure forms (i.e. the enantiomeric excess is equal to or higher than 95%).

In case the absolute stereochemical configuration of the asymmetric carbon atom(s) was not experimentally determined, the stereochemically isomeric form which was first isolated is designated as "A" and the second as "B", without further reference to the actual stereochemical configuration. Said "A" and "B" forms of those compounds of formula (I) wherein two stereogenic carbon atoms are present were separated in their pure stereochemically isomeric forms and designated as "A1" and "A2", and "B1" and "B2", without further reference to the actual stereochemical configuration.

Some of the compounds of formula (I) and (II) may also exist in their tautomeric forms. Such forms although not explicitly indicated in the above formula are intended to be included within the scope of the present invention. In particular, compounds of formula (I) wherein R$^3$ is hydrogen and compounds of formula (II) wherein R$^{13}$ is hydrogen may exist in their corresponding tautomeric form.

In particular, the present invention is concerned with the use of a compound of formula (I) and (II) wherein Het, respectively Het$^1$ is optionally substituted imidazolyl or triazolyl, in particular, 1-imidazolyl optionally substituted with $C_{1-6}$aLkyl or aryl; 2-imidazolyl optionally substituted with $C_{1-6}$alkyl; 5-imidazolyl optionally substituted with $C_{1-6}$alkyl; 1,3,4-triazol-1-yl and 1,2,4-triazol-1-yl.

Also of special interest are those compounds of formula (I) wherein

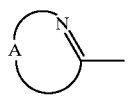

represents a radical of formula (b), particularly those wherein
  X represents O or S; and
  —R$^6$—R$^7$— represents a bivalent radical of formula (b-1);
thus being a N-[4-(heteroaryl-methyl)phenyl]-benzothiazolamine or a N-[4-(heteroaryl-methyl)phenyl]-benzoxazolamine.

Other compounds of special interest are those compounds of formula (I) wherein R$^2$ represents $C_{1-12}$alkyl; $C_{3-7}$cycloalkyl; aryl or $C_{1-12}$alkyl substituted with mono- or di($C_{1-4}$alkyl)amino, $C_{1-4}$alkyloxycarbonyl or aryloxy.

Particular compounds are those compounds of special interest wherein Het is 1-imidazolyl optionally substituted with $C_{1-6}$alkyl or aryl; 2-imidazolyl optionally substituted with $C_{1-6}$alkyl; 5-imidazolyl optionally substituted with $C_{1-6}$alkyl; 1,3,4-triazol-1-yl and 1,2,4-triazol-1-yl; R$^2$ represents $C_{1-12}$aLkyl; $C_{3-7}$cycloalkyl; aryl or $C_{1-12}$alkyl substituted with mono- or di($C_{1-4}$alkyl)amino; and

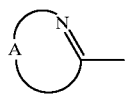

represents a radical of formula

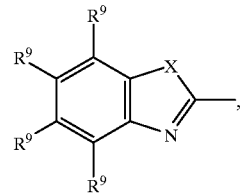

wherein X represents O or S.

Preferred compounds are those compounds of formula (I) wherein R$^1$ is hydrogen and R$^2$ is $C_{3-7}$cycloalkyl or $C^{1-6}$aLkyl optionally substituted with di($C_{1-6}$alkyl)amino.

Most preferred are the compounds
N-[4-[2-ethyl-1-(1H-imidazol-1-yl)butyl]phenyl]-2-benzothiazolamine;
N-[4-[2-ethyl-1-(1H-1,2,4-triazol-1-yl)butyl]phenyl]-2-benzoxazolamine;
N-[4-[2-ethyl-1-(1H-1,2,4-triazol-1-yl)butyl]phenyl]-2-benzothiazolamine;

N-[4-[2-(dimethylamino)-1-(1H-imidazol-1-yl)propyl]phenyl]-2-benzothiazolamine;

N-[4-[2-(dimethylamino)-1-(1H-1,2,4-triazol-1-yl)propyl]phenyl]-2-benzo-thiazolamine;

N-[4-[2-ethyl-1-(1H-imidazol-1-yl)butyl]phenyl]-2-benzoxazolamine;

N-[4-[2-ethyl-1-(1H-imidazol-1-yl)butyl]phenyl]-6-methoxy-2-benzothiazolamine;

N-[4-[2-(dimethylamino)-1-(1H-imidazol-1-yl)-2-methylpropyl]phenyl]-2-benzo-thiazolamine;

N-[4-[2-(dimethylamino)-2-methyl-1-(1H-1,2,4-triazol-1-yl)propyl]phenyl]-2-benzo-thiazolamine;

N-[4-[cyclohexyl(1H-imidazol-1-yl)methyl]phenyl]-2-benzothiazolamine;

N-[4-[cyclohexyl(1H-1,2,4-triazol-1-yl)methyl]phenyl]-2-benzothiazolamine; the

N-oxides, the stereochemically isomeric forms and the pharmaceutically acceptable addition salts thereof, especially (B1)-N-[4-[2-(dimethylamino)-1-(1H-imidazol-1-yl)propyl]-phenyl]-2-benzothiazolamine and (B)-N-[4-[2-ethyl-1-(1H-1,2,4-triazol-1-yl)butyl]phenyl]-2-benzothiazolamine.

The preparation of the compounds of formula (I) is described in WO 97/49704. The preparation of the compounds of formula (II) is described in EP application 97203886.3.

In particular, the compounds of formula (1) can generally be prepared by reacting an intermediate of formula (I-1) wherein $W^1$ is an appropriate leaving group such as, for example, a halogen, hydroxy or an alkylsulfonyloxy group, with an intermediate of formula (I-2) or a finctional derivative thereof. For instance, a functional derivative of imidazole may be 1,1'-carbonyldiimidazole.

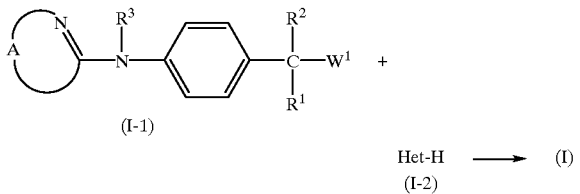

(I-1)

Het-H   ⟶   (I)
(I-2)

Said reaction may be performed in a reaction-inert solvent such as, for example, acetonitrile or tetrahydrofuran, in the presence of a suitable base such as, for example, potassium carbonate. In case $W^1$ is an hydroxy group, it may be convenient to perform the above reaction in the presence of triphenylphosphine and diethyl azodicarboxylate or a functional derivative of any of said reagents.

Alternatively, compounds of formula (I) may be prepared by N-alkylation of an intermediate of formula (I-3) with an intermediate of formula (I-4) wherein $W^2$ is an appropriate leaving group such as, for example, a phenoxy group, in a reaction-inert solvent such as , for example, N,N-dimethylformamide.

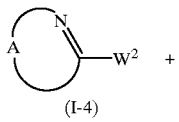

(I-4)

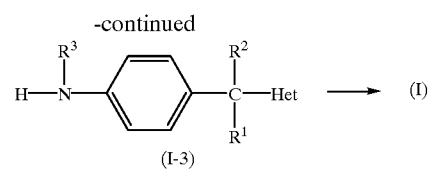

(I-3)

Further, the compounds of formula (II) can be prepared by reacting an intermediate of formula (I-1) wherein $W^1$ is an appropriate leaving group such as, for example, a halogen, hydroxy or an alkylsulfonyloxy group, with an intermediate of formula (II-2) or a functional derivative thereof. For instance, a functional derivative of imidazole may be 1,1'-carbonyldjirnidazole.

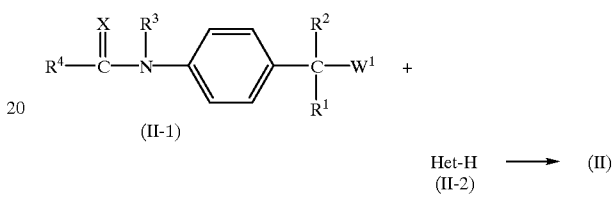

(II-1)

Het-H   ⟶   (II)
(II-2)

Said reaction may be performed in a reaction-inert solvent such as, for example, acetonitrile, dichloromethane or tetrahydrofuran, in the presence of a suitable base such as, for example, potassium carbonate. In case $W^1$ is an hydroxy group, it may be convenient to perform the above reaction in the presence of triphenylphosphine and diethyl azodicarboxylate or a functional derivative of any of said reagents, or in the presence of 1-hydroxy-1H-benzotriazole and dicyclohexylcarbodiimide.

Alternatively, compounds of formula (II) may be prepared by N-alkylation of an intermediate of formula (II-3) with an intermediate of formula (II-4) wherein $W^2$ is an appropriate leaving group such as, for example, hydroxy, a phenoxy group or a halogen, in a reaction-inert solvent such as , for example, water, N,N-dimethylformamide, dichloromethane, 1,2-dichloroethane, chloroform, N,N-dimethylacetamide, 2-propanone, benzene or the like, and optionally in the presence of a suitable base such as, for example, triethylamnine, pyridine or sodiumcarbonate.

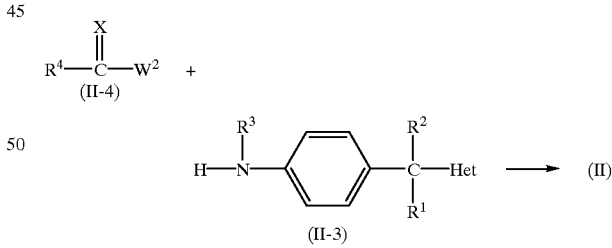

(II-4)

(II-3)

Also functional derivatives of intermediates of formula (II-4) may be used such as, for example, an anhydride, e.g. glutaric anhydride, dihydro-2H-pyran-2,6(3H)-dione, acetic acid anhydride; a cyanate; a thiocyanate; an isocyanate or an isothiocyanate. In some instances, it may be convenient to add an acid to the reaction medium such as, for instance, acetic acid may be used together with a cyanate.

As mentioned hereinabove, the invention relates to a therapy involving a retinoic acid metabolism blocking agent, more in particular a compound of formula (I) or formula (II), and especially N-[4-(heteroaryl-methyl)phenyl]-benzothiazolamines, in combination with a tocopherol, in particular vitamin E or a prodrug thereof. For both types of therapy, the active ingredients each independently may be administered orally, rectally, topically, percutaneously or by parenteral injection, depending on the affliction to be treated and the evaluation of the physician prescribing the treatment with the subject drugs.

Preferably, the drugs each independently are administered orally.

The retinoic acid metabolism blocking agent (RAMBA), interestingly the compounds of formula (I) or formula (II), more in particular a N-[4-(heteroaryl-methyl)phenyl]-benzothiazolarnine, and a tocopherol, more in particular vitamin E, or a prodrug thereof may be administered separately (i.e. simultaneously, concurrently or consecutively) or the different drugs may be combined in one dosage form.

A particular embodiment of the invention relates to a product containing (a) a pharmaceutical composition containing an effective amount of a tocopherol, in particular vitamin E or a prodrug thereof and (b) a pharmaceutical composition containing an effective amount of a retinoic acid metabolism blocking agent (RAMBA), in particular a compound of formula (I) or formula (II), an N-oxide, an addition salt or a stereochemically isomeric form thereof, as a combined preparation for simultaneous, separate or sequential use in pathological conditions, in particular, cancer or psoriasis therapy.

Another embodiment of the present invention encompasses the topical application of a tocopherol, more particularly vitamin E, or a prodrug thereof while taking the retinoic acid metabolism blocking agent (RAMBA) orally.

Preferentially, the product contains (a) a pharmaceutical composition containing an effective amount of a tocopherol, more particularly vitamin E or a prodrug thereof and (b) a pharmaceutical composition containing an effective amount of a retinoic acid metabolism blocking agent, more particularly a compound of formula (I) or formula (II). Such products may comprise, for example, a kit comprising a container with a suitable composition containing vitamin E and another container comprising a compound of formula (I) or formula (II), an N-oxide, an addition salt or a stereochemically isomeric form thereof. Such a product may have the advantage that a physician can select on the basis of the diagnosis the appropriate amounts of each component and the sequence and timing of the administration thereof.

Whether or not the retinoic acid metabolism blocking agent and the tocopherol, in particular vitamin E, or a prodrug thereof are administered separately or together, the drugs are preferably formulated in specific compositions thereof. As appropriate compositions there may be cited all compositions usually employed for systemically or topically administering drugs. To prepare the pharmaceutical compositions of this invention, an effective amount of the active ingredients is combined in intimate admixture with a pharmaceutically acceptable carrier, which carrier may take a wide variety of forms depending on the form of preparation desired for administration. For example, in preparing the compositions in oral dosage form, any of the usual pharmaceutical media may be employed such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. As appropriate compositions for topical application there may be cited all compositions usually employed for topically administering drugs, e.g. creams, gels, dressings, shampoos, tinctures, pastes, ointments, salves, powders and the like. Application of said compositions may be by aerosol, e.g. with a propellant such as nitrogen carbon dioxide, a freon, or without a propellant such as a pump spray, drops, lotions, or a semisolid such as a thickened composition which can be applied by a swab.

In order to enhance the solubility and/or the stability of the compounds of formula (I) or formula (II) in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin. Acid or base addition salts of compounds of formula (I) or formula (II) due to their increased water solubility over the corresponding base or acid form, are obviously more suitable in the preparation of aqueous compositions. Also co-solvents such as alcohols may improve the solubility and/or the stability of the compounds of formula (I) or formula (II) in pharmaceutical compositions.

For systemic administration, it is advantageous to formulate the aforementioned pharmaceutical compositions in dosage unit form for ease of administration and uniformity of dosage. Dosage unit form as used herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powders packets, wafers, injectable solutions or suspensions, teaspoonfuls, tablespoonfuls and the like, and segregated multiples thereof.

The dose of both the retinoic acid metabolism blocking agent, in particular the compound of formula (I) or formula (II) and the tocopherol, in particular, vitamin E or a prodrug thereof and the frequency of administration required will generally depend not only on the identity of the compound of formula (I) or of formula (II) and on the type of tocopherol or the type of prodrug thereof, but also on the physiology of the patient. The dose administered will generally be determined by a physician bearing in mind the age, weight, anticipated response and medical history of the patient.

In general it is contemplated that an effective daily dose of a retinoic acid metabolism blocking agent, in particular, a compound of formula (I) or of formula (II), an N-oxide, an addition salt or a stereochemically isomeric form thereof would be from 0.001 mg/kg to 20 mg/kg body weight and more preferably from 0.01 mg/kg to 10 mg/kg body weight.

Amounts of vitamin E are often expressed in I.U. (International Units). For the frequently used derivatives of vitamin E the conversion is as follows 1 mg dl-alpha-tocopherol acetate equals 1 I.U.

1 mg dl-alpha-tocopherol equals 1.1 1.U.

1 mg d-alpha-tocopherol acetate equals 1.36 I.U.

1 mg d-alpha-tocopherol equals 1.49 I.U.

The effective daily dose of vitamin E according to the present invention ranges from about 200 I.U. to 2400 I.U.. An interesting range for the effective daily dose of vitamin E goes from about 400 I.U. to about 1800 I.U. . Preferred range for the effective daily dose of vitamin E goes from about 600 I.U. to about 1600 I.U. Most preferred effective daily dose of vitamin E is 800 I.U. It may be appropriate to administer the required dose as several sub-doses at appropriate intervals throughout the day.

Experimental Part

Active ingredient (A.I.) as used throughout the examples directed towards formulations relates to a compound of formula (I)or formula (II), an N-oxide, a pharmaceutically acceptable addition salt or a stereochemically isomeric form thereof.

Example 1: CAPSULES 20 g of A.I., 0.2 g of vitamin E, 2,6 g sodium lauryl sulfate, 56 g starch, 56 g lactose, 0.8 g colloidal silicon dioxide, and 1.2 g magnesium stearate were vigorously stirred together. The resulting mixture was subsequently filled into 1000 suitable hardened gelatin capsules, each comprising 20 mg of A.I. and 0.2 mg of vitamin E.

Example 2: INJECTABLE SOLUTION 0.5 mg A.I. 1 and 0.05 mg vitamin E, 50 mg glucose anhydrous and 0.332 ml concentrated hydrochloric acid were mixed with 0.8 ml water for injections. Sodium hydroxide was added until pH=3.2±0.1 and water was added to 1 ml. The solution was sterilized and filled in sterile containers.

What is claimed:

1. The combination of a tocopherol and a retinoic acid metabolism blocking agent of formula (I) or (II)

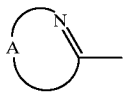

an N-oxide, a pharmaceutically acceptable addition salt or a stereochemically isomeric form thereof, wherein:

$R^1$ represents hydrogen, hydroxy, $C_{1-6}$alkyl or aryl;

$R^2$ represents hydrogen; $C_{1-12}$alkyl; $C_{3-7}$cycloalkyl; $C_{2-8}$alkenyl; aryl; pyrrolidinyl optionally substituted with $C_{1-4}$alkyl or $C_{1-4}$alkyloxycarbonyl; or $C_{1-12}$alkyl substituted with one or two substituents selected from $C_{3-7}$cycloalkyl, hydroxy, $C_{1-4}$alkyloxy, cyano, amino, mono- and di($C_{1-4}$alkyl)amino, mono- and di(aryl)amino, aryl$C_{1-4}$alkylamino, ($C_{1-4}$alkyl)(aryl$C_{1-4}$alkyl)amino, pyrrolidinyl , piperidinyl, piperazinyl optionally substituted with $C_{1-4}$alkyl, morpholinyl, perhydro-azepinyl, carboxyl, $C_{1-4}$alkyloxycarbonyl, aminocarbonyl, mono- and di ($C_{1-4}$alkyl)aminocarbonyl, aryl, aryloxy and arylthio;

$R^3$ represents hydrogen, $C_{1-6}$alkyl, aryl or $C_{1-6}$alkyl substituted with aryl;

Het represents an unsaturated heterocycle selected from imidazolyl, triazolyl, tetrazolyl and pyridinyl; each of said unsaturated heterocycles may optionally be substituted with amino, mercapto, $C_{1-6}$alkyl, $C_{1-6}$alkylthio or aryl;

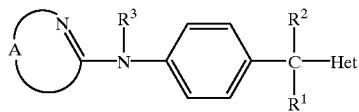

or

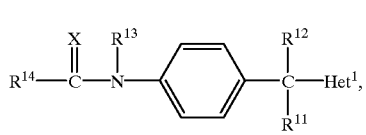

represents an unsaturated mono- or bicyclic heterocycle selected from the group consisting of pyridinyl, pyridazinyl, pyrimidinyl, pyrazinyl, quinolinyl, isoquinolinyl, purinyl, phtalazinyl, cinnolinyl, quinazolinyl and quinoxalinyl; each of said unsaturated mono- or bicyclic heterocycles may optionally be substituted with one, two or three substituents selected from hydroxy, halo, nitro, amino, $C_{1-6}$alkyl, hydroxy$C_{1-6}$alkyl, halo$C_{1-6}$alkyl, $C_{1-6}$alkyloxy, $C_{1-6}$alkylthio, formyl, carboxyl, mono- or di($C_{1-6}$alkyl)amino, $C_{1-6}$alkyloxycarbonyl or aryl; or

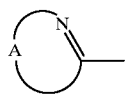

represents a radical of formula

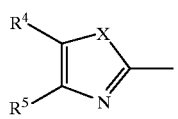

(a)

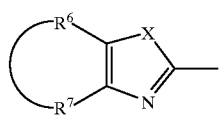

(b)

wherein:

each X independently represents $NR^8$, O, S, S(=O) or $S(=O)_2$;

wherein $R^8$ is hydrogen, $C_{1-6}$alkyl, aryl or aryl$C_{1-6}$alkyl;

$R^4$ and $R^5$ each independently represent hydrogen, hydroxy, halo, cyano, nitro, amino, $C_{1-6}$alkyl, hydroxy$C_{1-6}$alkyl, halo$C_{1-6}$alkyl, $C_{1-6}$alkyloxy, formyl, carboxyl, mono- or di($C_{1-6}$alkyl)amino, $C_{1-6}$alkyloxycarbonyl or aryl;

—$R^6$—$R^7$— represents a bivalent radical of formula

| | |
|---|---|
| —$CR^9$=$CR^9$—$CR^9$=$CR^9$— | (b-1); |
| —N=$CR^9$—$CR^9$=$CR^9$— | (b-2); |
| —$CR^9$=N—$CR^9$=$CR^9$— | (b-3); |
| —$CR^9$=$CR^9$—N=$CR^9$— | (b-4); |
| —$CR^9$=$CR^9$—$CR^9$=N— | (b-5); |
| —$CR^9$=N—N=$CR^9$— | (b-6); |
| —$CR^9$=N—$CR^9$=N— | (b-7); |

—CR⁹=CR⁹—N=N— (b-8);

—N=N—CR⁹=CR⁹— (b-9);

—N=CR⁹—N=CR⁹— (b-10);

—N=CR⁹—CR⁹=N— (b-11);

—CR⁹=N—N=N— (b-12);

—N=CR⁹—N=N— (b-13);

—N=N—CR⁹=N— (b-14);

or

—N=N—N=CR⁹— (b-15);

wherein each R⁹ independently represents hydrogen, hydroxy, halo, nitro, amino, $C_{1-6}$alkyl, hydroxy$C_{1-6}$alkyl, halo$C_{1-6}$alkyl, $C_{1-6}$alkyloxy, formyl, carboxyl, mono- or di($C_{1-6}$alkyl)amino, $C_{1-6}$alkyloxycarbonyl or aryl; and aryl represents phenyl or phenyl substituted with one, two or three substituents selected from hydroxy, halo, cyano, amino, mono- or di($C_{1-6}$alkyl)amino, $C_{1-6}$alkyl, halo$C_{1-6}$alkyl, hydroxy$C_{1-6}$alkyl, $C_{1-6}$alkyloxy, formyl, carboxyl and $C_{1-6}$alkylcarbonyl; or two adjacent carbon atoms on said phenyl may be substituted by a single bivalent radical having the formula $C_{1-12}$alkanediyl or halo$C_{1-12}$alkanediyl;

X represents O, S or NR¹³;

R¹¹ represents hydrogen, hydroxy, $C_{1-6}$alkyl or aryl¹;

R¹² represents hydrogen; $C_{1-12}$alkyl; $C_{3-7}$cycloalkyl; $C_{2-8}$alkenyl; aryl¹; Het²; or $C_{1-12}$alkyl substituted with one or two substituents selected from $C_{3-7}$cycloalkyl, hydroxy, $C_{1-4}$alkyloxy, cyano, amino, mono- and di($C_{1-4}$alkyl)amino, mono- or di(aryl¹$C_{1-4}$alkyl)amino, di (aryl¹$C_{1-4}$alkyl) aminocarbonyloxy, ($C_{1-4}$alkyl) (aryl¹$C_{1-4}$alkyl) amino, mono- and di (aryl¹) amino, ($C_{1-4}$alkyl)(di($C_{1-4}$alkyl)amino$C_{1-4}$alkyl)amino, pyrrolidinyl, piperidinyl, piperazinyl optionally substituted with $C_{1-4}$alkyl, morpholinyl, perhydro-azepinyl, carboxyl, $C_{1-4}$alkyloxycarbonyl, aminocarbonyl, mono- and di ($C_{1-4}$alkyl) aminocarbonyl, aryl¹, aryl¹oxy and aryl¹thio; or R¹¹ and R¹² taken together may form a bivalent radical of formula —R¹¹—R¹²— wherein —R¹¹—R¹²— represents —(CH₂)ₙ—wherein n is 2, 3, 4, 5 or 6;

R¹³ represents hydrogen, $C_{1-6}$alkyl, aryl¹, Het² or $C_{1-6}$alkyl substituted with aryl¹ or Het²;

R¹⁴ represents hydrogen; hydroxy; mercapto; $C_{1-6}$alkyloxy; $C_{1-6}$alkylthio; aryl¹oxy; aryl¹thio; Het²-oxy; Het²-thio; $C_{1-12}$alkyl optionally substituted with one, two or three substituents each independently selected from halo, thiolanyl, thienyl, dioxolanyl, isoxazolyl, oxazolyl, isothiazolyl, thiazolyl, isoxazolidinyl, oxazolidinyl, isothiazolidinyl, thiazolidinyl, piperidinyl, pyridinyl, piperazinyl, pyridazinyl, pyrimidinyl, pyrazinyl, 1,2,3-triazinyl, 1,2,4-triazinyl, tetrahydropyranyl, pyranyl, morpholinyl and dioxanyl; each of said monocyclic heterocycles may be optionally substituted with one or two substituents each independently selected from $C_{1-4}$alkyl, hydroxy, amino, halo, aryl, arylcarbonyl or $C_{1-4}$alkyloxycarbonyl; or a bicyclic heterocycle selected from indolinyl, indolyl, indazolyl, benzimidazolyl, benzotriazolyl, benzofuranyl, benzothienyl, 2H-1-benzopyranyl, 3,4-dihydro-2H-1-benzopyranyl, benzthiazolyl, isoquinolinyl, quinolinyl, 3,4-dihydroquinolinyl, cinnolinyl, quinazolinyl, quinoxalinyl, chromanyl, 1,4-benzodioxinyl, 1,4-benzoxathianyl, benzodioxanyl and benzodioxolanyl; each of said bicyclic heterocycles may be substituted with one or two substituents each independently selected from $C_{1-4}$alkyl, hydroxy, amino, halo, aryl, arylcarbonyl or $C_{1-4}$alkyloxycarbonyl.

2. A pharmaceutical composition comprising a pharmaceutically acceptable carrier and as active ingredients (a) an effective amount of a tocopherol or a prodrug thereof and (b) an effective amount a retinoic acid metabolism blocking agent of formula (I) or (II)

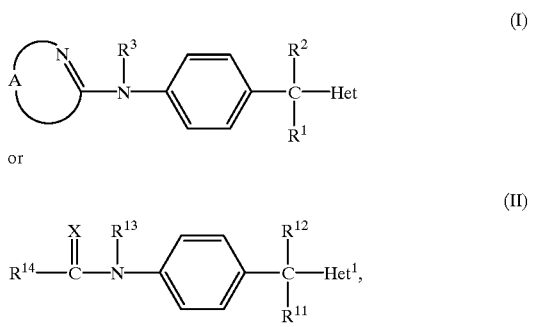

an N-oxide, a pharmaceutically acceptable addition salt or a stereochemically isomeric form thereof, wherein:

R¹ represents hydrogen, hydroxy, $C_{1-6}$alkyl or aryl;

R² represents hydrogen; $C_{1-12}$alkyl; $C_{3-7}$cycloalkyl; $C_{2-8}$alkenyl; aryl; pyrrolidinyl optionally substituted with hydroxy, mercapto, $C_{1-6}$alkyloxy, $C_{1-6}$alkylthio, aryl¹oxy, aryl¹thio, Het²-oxy, Het²-thio, $C_{3-7}$cycloalkyl optionally substituted with hydroxycarbonyl$C_{1-6}$alkyl, carboxyl, $C_{1-6}$alkyloxycarbonyl, aryl¹$C_{1-6}$alkyloxy, aryl¹$C_{1-6}$alkylthio, aryl¹, Het²; $C_{2-8}$alkenyl optionally substituted with one, two or three substituents selected from halo, $C_{3-7}$cycloalkyl, aryl¹, Het²; $C_{2-8}$alkynyl optionally substituted with halo, $C_{3-7}$cycloalkyl, aryl¹; $C_{3-7}$cycloalkyl optionally substituted with $C_{1-6}$alkyl or aryl¹; $C_{5-7}$cycloalkenyl optionally substituted with $C_{1-6}$alkyl or aryl¹; aryl¹; Het²; or

or

wherein Alk represents $C_{1-6}$alkanediyl; and

R¹⁵ represents hydrogen, $C_{1-6}$alkyl, aryl¹, Het², (aryl¹ or Het²)$C_{1-6}$alkyl, (aryl¹ or Het²)carbonyl or (aryl¹ or Het²) $C_{1-6}$alkyloxycarbonyl;

aryl¹ represents indanyl, indenyl, naphtyl, 5,6,7,8-tetrahydro-2-naphtalenyl, phenyl; said indanyl, indenyl, naphtyl or phenyl may be substituted with one, two, three, four or five substituents each independently selected from hydroxy, halo, nitro, cyano, amino, azido, mono- or di($C_{1-6}$alkyl)-amino, $C_{1-6}$alkylcarbonylamino, $C_{1-6}$alkyl, polyhalo$C_{1-6}$alkyl, hydroxy$C_{1-6}$alkyl, phenyl, phenyloxy, phenyl$C_{1-6}$alkyloxy, pyridinyl$C_{1-6}$alkyloxy, $C_{1-6}$alkyloxy, formyl, carboxyl and $C_{1-6}$alkylcarbonyl; or two adjacent carbon atoms on said phenyl may be substituted by a single bivalent radical having the formula $C_{1-12}$alkanediyl or polyhalo$C_{1-12}$alkanediyl;

Het¹ represents an unsaturated heterocycle selected from pyrrolyl, pyrazolyl, imidazolyl, triazolyl, tetrazolyl and pyridinyl; each of said unsaturated heterocycles may optionally be substituted with amino, mercapto, $C_{1-6}$alkyl, $C_{1-6}$alkylthio or aryl; and $Het^2$ represents a monocyclic heterocycle selected from pyrrolidinyl, pyrrolyl, pyrazolyl, imidazolyl, 1,3,4-triazolyl, 1,2,4-triazolyl, tetrahydrofuranyl, furanyl, $C_{1-4}$alkyl or $C_{1-4}$alkyloxycarbonyl; or $C_{1-12}$alkyl substituted with one or two substituents selected from $C_{3-7}$cycloalkyl, hydroxy, $C_{1-4}$alkyloxy, cyano, amino, mono- and di($C_{1-4}$alkyl)amino, mono- and di(aryl)amino, aryl$C_{1-4}$alkylamino, ($C_{1-4}$alkyl)(aryl$C_{1-4}$alkyl)amino, pyrrolidinyl, piperidinyl, piperazinyl optionally substituted with $C_{1-4}$alkyl, morpholinyl, perhydro-azepinyl, carboxyl, $C_{1-4}$alkyloxycarbonyl, aminocarbonyl, mono- and di($C_{1-4}$alkyl)aminocarbonyl, aryl, aryloxy and arylthio;

$R^3$ represents hydrogen, $C_{1-6}$alkyl, aryl or $C_{1-6}$alkyl substituted with aryl;

Het represents an unsaturated heterocycle selected from imidazolyl, triazolyl, tetrazolyl and pyridinyl; each of said unsaturated heterocycles may optionally be substituted with amino, mercapto, $C_{1-6}$alkyl, $C_{1-6}$alkylthio or aryl;

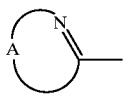

represents an unsaturated mono- or bicyclic heterocycle selected from the group consisting of pyridinyl, pyridazinyl, pyrimidinyl, pyrazinyl, quinolinyl, isoquinolinyl, purinyl, phtalazinyl, cinnolinyl, quinazolinyl and quinoxalinyl; each of said unsaturated mono- or bicyclic heterocycles may optionally be substituted with one, two or three substituents selected from hydroxy, halo, nitro, amino, $C_{1-6}$alkyl, hydroxy$C_{1-6}$alkyl, halo$C_{1-6}$alkyl, $C_{1-6}$alkyloxy, $C_{1-6}$alkylthio, formyl, carboxyl, mono- or di($C_{1-6}$alkyl)amino, $C_{1-6}$alkyloxycarbonyl or aryl; or

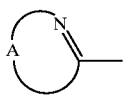

represents a radical of formula

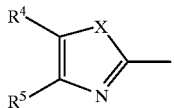

(a)

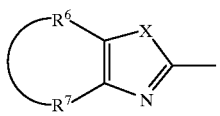

(b)

wherein:
each X independently represents $NR^8$, O, S, S(=O) or $S(=O)_2$;
wherein $R^8$ is hydrogen, $C_{1-6}$alkyl, aryl or aryl$C_{1-6}$alkyl;
$R^4$ and $R^5$ each independently represent hydrogen, hydroxy, halo, cyano, nitro, amino, $C_{1-6}$alkyl, hydroxy$C_{1-6}$alkyl, halo$C_{1-6}$alkyl, $C_{1-6}$alkyloxy, formyl, carboxyl, mono- or di($C_{1-6}$alkyl)amino, $C_{1-6}$alkyloxycarbonyl or aryl;

—$R^6$—$R^7$— represents a bivalent radical of formula:

| | |
|---|---|
| —$CR^9$=$CR^9$—$CR^9$=$CR^9$— | (b-1); |
| —N=$CR^9$—$CR^9$=$CR^9$— | (b-2); |
| —$CR^9$=N—$CR^9$=$CR^9$— | (b-3); |
| —$CR^9$=$CR^9$—N=$CR^9$— | (b-4); |
| —$CR^9$=$CR^9$—$CR^9$=N— | (b-5); |
| —$CR^9$=N—N=$CR^9$— | (b-6); |
| —$CR^9$=N—$CR^9$=N— | (b-7); |
| —$CR^9$=$CR^9$—N=N— | (b-8); |
| —N=N—$CR^9$=$CR^9$— | (b-9); |
| —N=$CR^9$—N=$CR^9$— | (b-10); |
| —N=$CR^9$—$CR^9$=N— | (b-11); |
| —$CR^9$=N—N=N— | (b-12); |
| —N=$CR^9$—N=N— | (b-13); |
| —N=N—$CR^9$=N— | (b-14) | or

| | |
|---|---|
| —N=N—N=$CR^9$— | (b-15); | wherein each $R^9$ independently represents hydrogen, hydroxy, halo, nitro, amino, $C_{1-6}$alkyl, hydroxy$C_{1-6}$alkyl, halo$C_{1-6}$alkyl, $C_{1-6}$alkyloxy, formyl, carboxyl, mono- or di($C_{1-6}$alkyl)amino, $C_{1-6}$alkyloxycarbonyl or aryl; and aryl represents phenyl or phenyl substituted with one, two or three substituents selected from hydroxy, halo, cyano, amino, mono- or di($C_{1-6}$alkyl)amino, $C_{1-6}$alkyl, halo$C_{1-6}$alkyl, hydroxy$C_{1-6}$alkyl, $C_{1-6}$alkyloxy, formyl, carboxyl and $C_{1-6}$alkylcarbonyl; or two adjacent carbon atoms on said phenyl may be substituted by a single bivalent radical having the formula $C_{1-12}$alkanediyl or halo$C_{1-12}$alkanediyl;

X represents O, S or $NR^{13}$;

$R^{11}$ represents hydrogen, hydroxy, $C_{1-6}$alkyl or $aryl^1$;

$R^{12}$ represents hydrogen; $C_{1-12}$alkyl; $C_{3-7}$cycloalkyl; $C_{2-8}$alkenyl; $aryl^1$; $Het^2$; or $C_{1-12}$alkyl substituted with one or two substituents selected from $C_{3-7}$cycloalkyl, hydroxy, $C_{1-4}$alkyloxy, cyano, amino, mono- and di($C_{1-4}$alkyl)amino, mono- or di($aryl^1C_{1-4}$alkyl)amino, di($aryl^1C_{1-4}$alkyl) aminocarbonyloxy, ($C_{1-4}$alkyl) ($aryl^1C_{1-4}$alkyl)amino, mono- and di($aryl^1$)amino, ($C_{1-4}$alkyl)(di ($C_{1-4}$alkyl)amino$C_{1-4}$alkyl)amino, pyrrolidinyl, piperidinyl, piperazinyl optionally substituted with $C_{1-4}$alkyl, morpholinyl, perhydro-azepinyl, carboxyl, $C_{1-4}$alkyloxycarbonyl, aminocarbonyl, mono- and di($C_{1-4}$alkyl)aminocarbonyl, $aryl^1$, $aryl^1$oxy and $aryl^1$thio;

or $R^{11}$ and $R^{12}$ taken together may form a bivalent radical of formula —$R^{11}$—$R^{12}$— wherein —$R^{11}$—$R^{12}$— represents —$(CH_2)_n$— wherein n is 2, 3, 4, 5 or 6;

R represents hydrogen, $C_{1-6}$alkyl, $aryl^1$, $Het^2$ or $C_{1-6}$alkyl substituted with $aryl^1$ or $Het^2$;

$R^{14}$ represents hydrogen; hydroxy; mercapto; $C_{1-6}$alkyloxy; $C_{1-6}$alkylthio; $aryl^1$oxy; $aryl^1$thio; $Het^2$-oxy; $Het^2$-thio; $C_{1-12}$alkyl optionally substituted with one, two or three substituents each independently selected from halo, hydroxy, mercapto, $C_{1-6}$alkyloxy, $C_{1-6}$alkylthio, $aryl^1$oxy, aryl¹¹thio, Het²-oxy, Het²-thio, C₃₋₇cycloalkyl optionally substituted with hydroxycarbonylC₁₋₆alkyl, carboxyl, C₁₋₆alkyloxycarbonyl, aryl¹C₁₋₆alkyloxy, aryl¹C₁₋₆alkylthio, aryl¹, Het²; C₂₋₈alkenyl optionally substituted with one, two or three substituents selected from halo, C₃₋₇cycloalkyl, aryl¹, Het²; C₂₋₈alkynyl optionally substituted with halo, C₃₋₇cycloalkyl, aryl¹; C₃₋₇cycloalkyl optionally substituted with C₁₋₆alkyl or aryl¹; C₅₋₇cycloalkenyl optionally substituted with C₁₋₆alkyl or aryl¹; aryl¹; Het²; or —Alk—NR¹³R¹⁵ (i)

or

—NR¹³R¹⁵ (ii)

wherein Alk represents C₁₋₆alkanediyl; and
R1⁵ represents hydrogen, C₁₋₆alkyl, aryl¹, Het², (aryl¹ or Het²)C₁₋₆alkyl, (aryl¹ or Het²)carbonyl or (aryl¹ or Het²) C₁₋₆alkyloxycarbonyl;
aryl¹ represents indanyl, indenyl, naphtyl, 5,6,7,8-tetrahydro-2-naphtalenyl, phenyl; said indanyl, indenyl, naphtyl or phenyl may be substituted with one, two, three, four or five substituents each independently selected from hydroxy, halo, nitro, cyano, amino, azido, mono- or di(C₁₋₆alkyl)-amino, C₁₋₆alkylcarbonylamino, C₁₋₆alkyl, polyhaloC₁₋₆alkyl, hydroxyC₁₋₆alkyl, phenyl, phenyloxy, phenylC₁₋₆alkyloxy, pyridinylC₁₋₆alkyloxy, C₁₋₆alkyloxy, formyl, carboxyl and C₁₋₆alkylcarbonyl; or two adjacent carbon atoms on said phenyl may be substituted by a single bivalent radical having the formula C₁₋₁₂alkanediyl or polyhaloC₁₋₁₂alkanediyl;
Het¹ represents an unsaturated heterocycle selected from pyrrolyl, pyrazolyl, imidazolyl, triazolyl, tetrazolyl and pyridinyl; each of said unsaturated heterocycles may optionally be substituted with amino, mercapto, C₁₋₆alkyl, C₁₋₆alkylthio or aryl; and
Het² represents a monocyclic heterocycle selected from pyrrolidinyl, pyrrolyl, pyrazolyl, imidazolyl, 1,3,4-triazolyl, 1,2,4-triazolyl, tetrahydrofuranyl, furanyl, thiolanyl, thienyl, dioxolanyl, isoxazolyl, oxazolyl, isothiazolyl, thiazolyl, isoxazolidinyl, oxazolidinyl, isothiazolidinyl, thiazolidinyl, piperidinyl, pyridinyl, piperazinyl, pyridazinyl, pyrimidinyl, pyrazinyl, 1,2,3-triazinyl, 1,2,4-triazinyl, tetrahydropyranyl, pyranyl, morpholinyl and dioxanyl; each of said monocyclic heterocycles may be optionally substituted with one or two substituents each independently selected from C₁₋₄alkyl, hydroxy, amino, halo, aryl, arylcarbonyl or C₁₋₄alkyloxycarbonyl; or a bicyclic heterocycle selected from indolinyl, indolyl, indazolyl, benzimidazolyl, benzotriazolyl, benzofuranyl, benzothienyl, 2H-1-benzopyranyl, 3,4-dihydro-2H-1-benzopyranyl, benzthiazolyl, isoquinolinyl, quinolinyl, 3,4-dihydroquinolinyl, cinnolinyl, quinazolinyl, quinoxalinyl, chromanyl, 1,4-benzodioxinyl, 1,4-benzoxathianyl, benzodioxanyl and benzodioxolanyl; each of said bicyclic heterocycles may be substituted with one or two substituents each independently selected from C₁₋₄alkyl, hydroxy, amino, halo, aryl, arylcarbonyl or C₁₋₄alkyloxycarbonyl.

3. A pharmaceutical composition as claimed in claim 10 comprising vitamin E and a N-[4-(heteroaryl-methyl) phenyl]-benzothiazolamine, an N-oxide, a pharmaceutically acceptable addition salt or a stereochemically isomeric form thereof.

4. A process for preparing a pharmaceutical composition as claimed in claim 2 comprising mixing an effective amount of the active ingredients with a carrier.

5. A product containing (a) a retinoic acid metabolism blocking agent of formula (I) or (II)

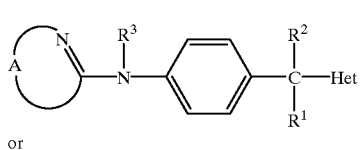

(I)

or

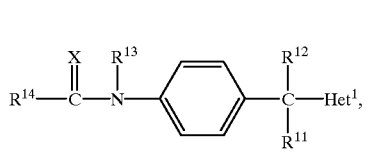

(II)

an N-oxide, a pharmaceutically acceptable addition salt or a stereochemically isomeric form thereof, wherein:

$R^1$ represents hydrogen, hydroxy, $C_{1-6}$alkyl or aryl;

$R^2$ represents hydrogen; $C_{1-12}$alkyl; $C_{3-7}$cycloalkyl; $C_{2-8}$alkenyl; aryl; pyrrolidinyl optionally substituted with $C_{1-4}$alkyl or $C_{1-4}$alkyloxycarbonyl; or $C_{1-12}$alkyl substituted with one or two substituents selected from $C_{3-7}$cycloalkyl, hydroxy, $C_{1-4}$alkyloxy, cyano, amino, mono- and di($C_{1-4}$alkyl)amino, mono- and di(aryl)amino, aryl$C_{1-4}$alkylamino, ($C_{1-4}$alkyl)(aryl$C_{1-4}$alkyl)amino, pyrrolidinyl, piperidinyl, piperazinyl optionally substituted with $C_{1-4}$alkyl, morpholinyl, perhydro-azepinyl, carboxyl, $C_{1-4}$alkyloxycarbonyl, aminocarbonyl, mono- and di($C_{1-4}$alkyl)aminocarbonyl, aryl, aryloxy and arylthio;

$R^3$ represents hydrogen, $C_{1-6}$alkyl, aryl or $C_{1-6}$alkyl substituted with aryl;

Het represents an unsaturated heterocycle selected from imidazolyl, triazolyl, tetrazolyl and pyridinyl; each of said unsaturated heterocycles may optionally be substituted with amino, mercapto, $C_{1-6}$alkyl, $C_{1-6}$alkylthio or aryl;

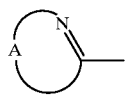

represents an unsaturated mono- or bicyclic heterocycle selected from the group consisting of pyridinyl, pyridazinyl, pyrimidinyl, pyrazinyl, quinolinyl, isoquinolinyl, purinyl, phtalazinyl, cinnolinyl, quinazolinyl and quinoxalinyl; each of said unsaturated mono- or bicyclic heterocycles may optionally be substituted with one, two or three substituents selected from hydroxy, halo, nitro, amino, $C_{1-6}$alkyl, hydroxy$C_{1-6}$alkyl, halo$C_{1-6}$alkyl, $C_{1-6}$alkyloxy, $C_{1-6}$alkylthio, formyl, carboxyl, mono- or di($C_{1-6}$alkyl)amino, $C_{1-6}$alkyloxycarbonyl or aryl; or

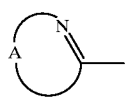

represents a radical of formula

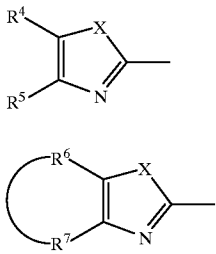

wherein:
each X independently represents $NR^8$, O, S, S(=O) or $S(=O)_2$;
wherein $R^8$ is hydrogen, $C_{1-6}$alkyl, aryl or aryl$C_{1-6}$alkyl;
$R^4$ and $R^5$ each independently represent hydrogen, hydroxy, halo, cyano, nitro, amino, $C_{1-6}$alkyl, hydroxy$C_{1-6}$alkyl, halo$C_{1-6}$alkyl, $C_{1-6}$alkyloxy, formyl, carboxyl, mono- or di($C_{1-6}$alkyl)amino, $C_{1-6}$alkyloxycarbonyl or aryl;
—$R^6$—$R^7$— represents a bivalent radical of formula:

$$-CR^9=CR^9-CR^9=CR^9- \qquad (b\text{-}1);$$
$$-N=CR^9-CR^9=CR^9- \qquad (b\text{-}2);$$
$$-CR^9=N-CR^9=CR^9- \qquad (b\text{-}3);$$
$$-CR^9=CR^9-N=CR^9- \qquad (b\text{-}4);$$
$$-CR^9=CR^9R^9=N- \qquad (b\text{-}5);$$
$$-CR^9=N-N=CR^9- \qquad (b\text{-}6);$$
$$-CR^9=N-CR^9=N- \qquad (b\text{-}7);$$
$$-CR^9=CR^9-N=N- \qquad (b\text{-}8);$$
$$-N=N-CR^9=CR^9- \qquad (b\text{-}9);$$
$$-N=CR^9-N=CR^9- \qquad (b\text{-}10);$$
$$-N=CR^9-CR^9=N- \qquad (b\text{-}11);$$
$$-CR^9=N-N=N- \qquad (b\text{-}12);$$
$$-N=CR^9-N=N- \qquad (b\text{-}13);$$
$$-N=N-CR^9=N- \qquad (b\text{-}14);$$

or $$-N=N-N=CR^9- \qquad (b\text{-}15);$$

wherein each $R^9$ independently represents hydrogen, hydroxy, halo, nitro, amino, $C_{1-6}$alkyl, hydroxy$C_{1-6}$alkyl, halo$C_{1-6}$alkyl, $C_{1-6}$alkyloxy, formyl, carboxyl, mono- or di($C_{1-6}$alkyl)amino, $C_{1-6}$alkyloxycarbonyl or aryl; and
aryl represents phenyl or phenyl substituted with one, two or three substituents selected from hydroxy, halo, cyano, amino, mono- or di($C_{1-6}$alkyl)amino, $C_{1-6}$alkyl, halo$C_{1-6}$alkyl, hydroxy$C_{1-6}$alkyl, $C_{1-6}$alkyloxy, formyl, carboxyl and $C_{1-6}$alkylcarbonyl; or two adjacent carbon atoms on said phenyl may be substituted by a single bivalent radical having the formula $C_{1-12}$alkanediyl or halo$C_{1-12}$alkanediyl;
X represents O, S or $NR^{13}$;

$R^{11}$ represents hydrogen, hydroxy, $C_{1-6}$alkyl or aryl$^1$;
$R^{12}$ represents hydrogen; $C_{1-12}$alkyl; $C_{3-7}$cycloalkyl; $C_{2-8}$alkenyl; aryl$^1$; Het$^2$; or $C_{1-12}$alkyl substituted with one or two substituents selected from $C_{3-7}$cycloalkyl, hydroxy, $C_{1-4}$alkyloxy, cyano, amino, mono- and di($C_{1-4}$alkyl)amino, mono- or di(aryl$^1C_{1-4}$alkyl)amino, di(aryl$^1C_{1-4}$alkyl)aminocarbonyloxy, ($C_{1-4}$alkyl) (aryl$^1C_{1-4}$alkyl)amino, mono- and di(aryl$^1$)amino, ($C_{1-4}$alkyl) (di($C_{1-4}$alkyl)amino$C_{1-4}$alkyl)amino, pyrrolidinyl, piperidinyl, piperazinyl optionally substituted with $C_{1-4}$alkyl, morpholinyl, perhydro-azepinyl, carboxyl, $C_{1-4}$alkyloxycarbonyl, aminocarbonyl, mono- and di($C_{1-4}$alkyl)aminocarbonyl, aryl$^1$, aryl$^1$oxy and aryl$^1$thio; or
$R^{11}$ and $R^{12}$ taken together may form a bivalent radical of formula —$R^{11}$—$R^{12}$— wherein —$R^{11}$—$R^{12}$— represents —$(CH_2)_n$—wherein n is 2, 3, 4, 5 or 6;
$R^{13}$ represents hydrogen, $C_{1-6}$alkyl, aryl$^1$, Het$^2$ or $C_{1-6}$alkyl substituted with aryl$^1$ or Het$^2$;
$R^{14}$ represents hydrogen; hydroxy; mercapto; $C_{1-6}$alkyloxy; $C_{1-6}$alkylthio; aryl$^1$oxy; aryl$^1$thio; Het$^2$-oxy; Het$^2$-thio; $C_{1-12}$alkyl optionally substituted with one, two or three substituents each independently selected from halo, hydroxy, mercapto, $C_{1-6}$alkyloxy, $C_{1-6}$alkylthio, aryl$^1$oxy, aryl$^1$thio, Het$^2$-oxy, Het$^2$-thio, $C_{3-7}$cycloalkyl optionally substituted with hydroxycarbonyl$C_{1-6}$alkyl, carboxyl, $C_{1-6}$alkyloxycarbonyl, aryl$^1C_{1-6}$alkyloxy, aryl$^1C_{1-6}$alkylthio, aryl$^1$, Het$^2$; $C_{2-8}$alkenyl optionally substituted with one, two or three substituents selected from halo, $C_{3-7}$cycloalkyl, aryl$^1$, Het$^2$; $C_{2-8}$alkynyl optionally substituted with halo, $C_{3-7}$cycloalkyl, aryl$^1$; $C_{3-7}$cycloalkyl optionally substituted with $C_{1-6}$alkyl or aryl$^1$; $C_{5-7}$cycloalkenyl optionally substituted with $C_{1-6}$alkyl or aryl$^1$; aryl$^1$; Het$^2$; or $$-Alk-NR^{13}R^{15} \qquad (i)$$

or $$-NR^{13}R^{15} \qquad (ii)$$

wherein Alk represents $C_{1-6}$alkanediyl; and
$R^{15}$ represents hydrogen, $C_{1-6}$alkyl, aryl$^1$, Het$^2$, (aryl$^1$ or Het$^2$)$C_{1-6}$alkyl, (aryl$^1$ or Het$^2$)carbonyl or (aryl$^1$ or Het$^2$) $C_{1-6}$alkyloxycarbonyl;
aryl$^1$ represents indanyl, indenyl, naphtyl, 5,6,7,8-tetrahydro-2-naphtalenyl, phenyl; said indanyl, indenyl, naphtyl or phenyl may be substituted with one, two, three, four or five substituents each independently selected from hydroxy, halo, nitro, cyano, amino, azido, mono- or di($C_{1-6}$alkyl)-amino, $C_{1-6}$alkylcarbonylamino, $C_{1-6}$alkyl, polyhalo$C_{1-6}$alkyl, hydroxy$C_{1-6}$alkyl, phenyl, phenyloxy, phenyl$C_{1-6}$alkyloxy, pyridinyl$C_{1-6}$alkyloxy, $C_{1-6}$alkyloxy, formyl, carboxyl and $C_{1-6}$alkylcarbonyl; or two adjacent carbon atoms on said phenyl may be substituted by a single bivalent radical having the formula $C_{1-12}$alkanediyl or polyhalo$C_{1-12}$alkanediyl;
Het1 represents an unsaturated heterocycle selected from pyrrolyl, pyrazolyl, imidazolyl, triazolyl, tetrazolyl and pyridinyl; each of said unsaturated heterocycles may optionally be substituted with amino, mercapto, $C_{1-6}$alkyl, $C_{1-6}$alkylthio or aryl; and
Het$^2$ represents a monocyclic heterocycle selected from pyrrolidinyl, pyrrolyl, pyrazolyl, imidazolyl, 1,3,4-triazolyl, 1,2,4-triazolyl, tetrahydrofuranyl, furanyl, thiolanyl, thienyl, dioxolanyl, isoxazolyl, oxazolyl, isothiazolyl, thiazolyl, isoxazolidinyl, oxazolidinyl, isothiazolidinyl, thiazolidinyl, piperidinyl, pyridinyl, piperazinyl, pyridazinyl, pyrimidinyl, pyrazinyl, 1,2,3-triazinyl, 1,2,4-triazinyl, tetrahydropyranyl, pyranyl, morpholinyl and dioxanyl; each of said monocyclic heterocycles may be optionally substituted with one or two substituents each independently selected from $C_{1-4}$alkyl, hydroxy, amino, halo, aryl, arylcarbonyl or $C_{1-4}$alkyloxycarbonyl; or a bicyclic heterocycle selected from indolinyl, indolyl, indazolyl, benzimidazolyl, benzotriazolyl, benzofuranyl, benzothienyl, 2H-1-benzopyranyl, 3,4-dihydro-2H-1-benzopyranyl, benzthiazolyl, isoquinolinyl, quinolinyl, 3,4-dihydroquinolinyl, cinnolinyl, quinazolinyl, quinoxalinyl, chromanyl, 1,4-benzodioxinyl, 1,4-benzoxathianyl, benzodioxanyl and benzodioxolanyl; each of said bicyclic heterocycles may be substituted with one or two substituents each independently selected from $C_{1-4}$alkyl, hydroxy, amino, halo, aryl, arylcarbonyl or $C_{1-4}$alkyloxycarbonyl; and (b) a tocopherol or a prodrug thereof, as a combined preparation for simultaneous, separate or sequential use in cancer therapy.

6. A product containing (a) a retinoic acid metabolism blocking agent of formula (I) or (II)

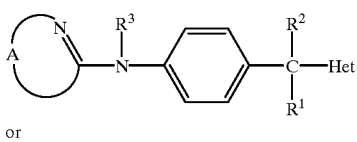

(I)

or

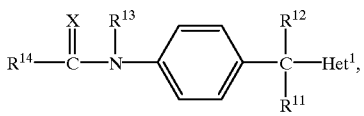

(II)

an N-oxide, a pharmaceutically acceptable addition salt or a stereochemically isomeric form thereof, wherein:

$R^1$ represents hydrogen, hydroxy, $C_{1-6}$alkyl or aryl;
$R^2$ represents hydrogen; $C_{1-12}$alkyl; $C_{3-7}$cycloalkyl; $C_{2-8}$alkenyl; aryl; pyrrolidinyl optionally substituted with $C_{1-4}$alkyl or $C_{1-4}$alkyloxycarbonyl; or $C_{1-12}$alkyl substituted with one or two substituents selected from $C_{3-7}$cycloalkyl, hydroxy, $C_{1-4}$alkyloxy, cyano, amino, mono- and di($C_{1-4}$alkyl)amino, mono- and di(aryl)amino, aryl$C_{1-4}$alkylamino, ($C_{1-4}$alkyl)(aryl$C_{1-4}$alkyl)amino, pyrrolidinyl, piperidinyl, piperazinyl optionally substituted with $C_{1-4}$alkyl, morpholinyl, perhydro-azepinyl, carboxyl, $C_{1-4}$alkyloxycarbonyl, aminocarbonyl, mono- and di($C_{1-4}$alkyl)aminocarbonyl, aryl, aryloxy and arylthio;
$R^3$ represents hydrogen, $C_{1-6}$alkyl, aryl or $C_{1-6}$alkyl substituted with aryl;
Het represents an unsaturated heterocycle selected from imidazolyl, triazolyl, tetrazolyl and pyridinyl; each of said unsaturated heterocycles may optionally be substituted with amino, mercapto, $C_{1-6}$alkyl, $C_{1-6}$alkylthio or aryl;

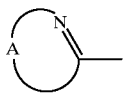

represents an unsaturated mono- or bicyclic heterocycle selected from the group consisting of pyridinyl, pyridazinyl, pyrimidinyl, pyrazinyl, quinolinyl, isoquinolinyl, purinyl, phtalazinyl, cinnolinyl, quinazolinyl and quinoxalinyl; each of said unsaturated mono- or bicyclic heterocycles may optionally be substituted with one, two or three substituents selected from hydroxy, halo, nitro, amino, $C_{1-6}$alkyl, hydroxy$C_{1-6}$alkyl, halo$C_{1-6}$alkyl, $C_{1-6}$alkyloxy, $C_{1-6}$alkylthio, formyl, carboxyl, mono- or di($C_{1-6}$alkyl)amino, $C_{1-6}$alkyloxycarbonyl or aryl; or

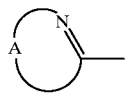

represent a radical of formula

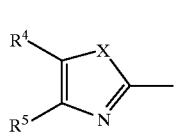

(a)

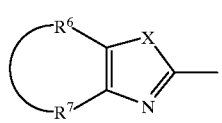

(b)

wherein
each X independently represents $NR^8$, O, S, S(=O) or $S(=O)_2$;
wherein $R^8$ is hydrogen, $C_{1-6}$alkyl, aryl or aryl$C_{1-6}$alkyl;
$R^4$ and $R^5$ each independently represent hydrogen, hydroxy, halo, cyano, nitro, amino, $C_{1-6}$alkyl, hydroxy$C_{1-6}$alkyl, halo$C_{1-6}$alkyl, $C_{1-6}$alkyloxy, formyl, carboxyl, mono- or di($C_{1-6}$alkyl)amino, $C_{1-6}$alkyloxycarbonyl or aryl;

—$R^6$—$R^7$— represents a bivalent radical of formula

| | |
|---|---|
| —$CR^9$=$CR^9$—$CR^9$=$CR^9$— | (b-1); |
| —N=$CR^9$—$CR^9$=$CR^9$— | (b-2); |
| —$CR^9$=N—$CR^9$=$CR^9$— | (b-3); |
| —$CR^9$=$CR^9$—N=$CR^9$— | (b-4); |
| —$CR^9$=$CR^9$—$CR^9$=N— | (b-5); |
| —$CR^9$=N—N=$CR^9$— | (b-6); |
| —$CR^9$=N—$CR^9$=N— | (b-7); |
| —$CR^9$=$CR^9$—N=N— | (b-8); |
| —N=N—$CR^9$=$CR^9$— | (b-9); |
| —N=$CR^9$—N=$CR^9$— | (b-10); |
| —N=$CR^9$—$CR^9$=N— | (b-11); |
| —$CR^9$=N—N=N— | (b-12); |
| —N=$CR^9$—N=N— | (b-13); |
| —N=N—$CR^9$=N— | (b-14) | or

| | |
|---|---|
| —N=N—N=$CR^9$— | (b-15); | wherein each $R^9$ independently represents hydrogen, hydroxy, halo, nitro, amino, $C_{1-6}$alkyl, hydroxy$C_{1-}$ $_6$alkyl, haloC$_{1-6}$alkyl, C$_{1-6}$alkyloxy, formyl, carboxyl, mono- or di(C$_{1-6}$alkyl)amino, C$_{1-6}$alkyloxycarbonyl or aryl; and aryl represents phenyl or phenyl substituted with one, two or three substituents selected from hydroxy, halo, cyano, amino, mono- or di(C$_{1-6}$alkyl)amino, C$_{1-6}$alkyl, haloC$_{1-6}$alkyl, hydroxyC$_{1-6}$alkyl, C$_{1-6}$alkyloxy, formyl, carboxyl and C$_{1-6}$alkylcarbonyl; or two adjacent carbon atoms on said phenyl may be substituted by a single bivalent radical having the formula C$_{1-12}$alkanediyl or haloC$_{1-12}$alkanediyl; X represents O, S or NR$^{13}$;

R$^{11}$ represents hydrogen, hydroxy, C$_{1-6}$alkyl or aryl$^1$;

R$^{12}$ represents hydrogen; C$_{1-12}$alkyl; C$_{3-7}$cycloalkyl; C$_{1-8}$alkenyl; aryl$^1$; Het$^2$; or C$_{1-12}$alkyl substituted with one or two substituents selected from C$_{3-7}$cycloalkyl, hydroxy, C$_{1-4}$alkyloxy, cyano, amino, mono- and di(C$_{1-4}$alkyl) amino, mono- or di(aryl$^1$C$_{1-4}$alkyl)amino, di (aryl$^1$C$_{1-4}$alkyl) aminocarbonyloxy, (C$_{1-4}$alkyl) (arylC$_{1-4}$alkyl) amino, mono- and di (aryl$^1$) amino, (C$_{1-4}$alkyl)(di(C$_{1-4}$alkyl)aminoC$_{1-4}$alkyl)amino, pyrrolidinyl, piperidinyl, piperazinyl optionally substituted with C$_{1-4}$alkyl, morpholinyl, perhydro-azepinyl, carboxyl, C$_{1-4}$alkyloxycarbonyl, aminocarbonyl, mono- and di (C$_{1-4}$alkyl) aminocarbonyl, aryl$^1$, aryl$^1$oxy and aryl$^1$thio; or R$^{11}$ and R$^{12}$ taken together may form a bivalent radical of formula —R$^{11}$—R$^{12}$— wherein —R$^{11}$—R$^{12}$— represents —(CH$_2$)$_n$—wherein n is 2, 3, 4, 5 or 6;

R$^{13}$ represents hydrogen, C$_{1-6}$alkyl, aryl$^1$, Het$^2$ or C$_{1-6}$alkyl substituted with aryl$^1$ or Het$^2$;

R$^{14}$ represents hydrogen; hydroxy; mercapto; C$_{1-6}$alkyloxy; C$_{1-6}$alkylthio; aryl$^1$oxy; aryl$^1$thio; Het$^2$-oxy; Het$^2$-thio; C$_{1-12}$alkyl optionally substituted with one, two or three substituents each independently selected from halo, hydroxy, mercapto, C$_{1-6}$alkyloxy, C$_{1-6}$alkylthio, aryl$^1$oxy, aryl$^1$thio, Het$^2$-oxy, Het$^2$-thio, C$_{3-7}$cycloalkyl optionally substituted with hydroxycarbonylC$_{1-6}$alkyl, carboxyl, C$_{1-6}$alkyloxycarbonyl, aryl$^1$C$_{1-6}$alkyloxy, aryl$^1$C$_{1-6}$alkylthio, aryl$^1$, Het$^2$; C$_{2-8}$alkenyl optionally substituted with one, two or three substituents selected from halo, C$_{3-7}$cycloalkyl, aryl$^1$, Het2; C$_{2-8}$alkynyl optionally substituted with halo, C$_{3-7}$cycloalkyl, aryl$^1$; C$_{3-7}$cycloalkyl optionally substituted with C$_{1-6}$alkyl or aryl$^1$;

C$_{5-7}$cycloalkenyl optionally substituted with C$_{1-6}$alkyl or aryl$^1$; aryl$^1$; Het$^2$; or —Alk—NR$^{13}$R$^{15}$ (i)

or

—NR$^{13}$R$^{15}$ (ii)

wherein Alk represents C$_{1-6}$alkanediyl; and

R$^{15}$ represents hydrogen, C$_{1-6}$alkyl, aryl$^1$, Het$^2$, (aryl$^1$ or Het$^2$)C$_{1-6}$alkyl, (aryl$^1$ or Het$^2$)carbonyl or (aryl$^1$ or Het$^2$) C$_{1-6}$alkyloxycarbonyl;

aryl$^1$ represents indanyl, indenyl, naphtyl, 5,6,7,8-tetrahydro-2-naphtalenyl, phenyl; said indanyl, indenyl, naphtyl or phenyl may be substituted with one, two, three, four or five substituents each independently selected from hydroxy, halo, nitro, cyano, amino, azido, mono- or di(C$_{1-6}$alkyl)-amino, C$_{1-6}$alkylcarbonylamino, C$_{1-6}$alkyl, polyhaloC$_{1-6}$alkyl, hydroxyC$_{1-6}$alkyl, phenyl, phenyloxy, phenylC$_{1-6}$alkyloxy, pyridinylC$_{1-6}$alkyloxy, C$_{1-6}$alkyloxy, formyl, carboxyl and C$_{1-6}$alkylcarbonyl; or two adjacent carbon atoms on said phenyl may be substituted by a single bivalent radical having the formula C$_{1-12}$alkanediyl or polyhaloC$_{1-12}$alkanediyl;

Het$^1$ represents an unsaturated heterocycle selected from pyrrolyl, pyrazolyl, imidazolyl, triazolyl, tetrazolyl and pyridinyl; each of said unsaturated heterocycles may optionally be substituted with amino, mercapto, C$_{1-6}$alkyl, C$_{1-6}$alkylthio or aryl; and Het$^2$ represents a monocyclic heterocycle selected from pyrrolidinyl, pyrrolyl, pyrazolyl, imidazolyl, 1,3,4-triazolyl, 1,2,4-triazolyl, tetrahydrofuranyl, furanyl, thiolanyl, thienyl, dioxolanyl, isoxazolyl, oxazolyl, isothiazolyl, thiazolyl, isoxazolidinyl, oxazolidinyl, isothiazolidinyl, thiazolidinyl, piperidinyl, pyridinyl, piperazinyl, pyridazinyl, pyrimidinyl, pyrazinyl, 1,2,3 triazinyl, 1,2,4-triazinyl, tetrahydropyranyl, pyranyl, morpholinyl and dioxanyl; each of said monocyclic heterocycles may be optionally substituted with one or two substituents each independently selected from C$_{1-4}$alkyl, hydroxy, amino, halo, aryl, arylcarbonyl or C$_{1-4}$alkyloxycarbonyl; or a bicyclic heterocycle selected from indolinyl, indolyl, indazolyl, benzimidazolyl, benzotriazolyl, benzofuranyl, benzothienyl, 2H-1-benzopyranyl, 3,4-dihydro-2H-1-benzopyranyl, benzthiazolyl, isoquinolinyl, quinolinyl, 3,4-dihydroquinolinyl, cinnolinyl, quinazolinyl, quinoxalinyl, chromanyl, 1,4-benzodioxinyl, 1,4-benzoxathianyl, benzodioxanyl and benzodioxolanyl; each of said bicyclic heterocycles may be substituted with one or two substituents each independently selected from C$_{1-4}$alkyl, hydroxy, amino, halo, aryl, arylcarbonyl or C$_{1-4}$alkyloxycarbonyl; and (b) a tocopherol or a prodrug thereof, as a combined preparation for simultaneous, separate or sequential use in psoriasis therapy.

7. A method for avoiding, alleviating, suppressing or overcoming the adverse side effects of therapy with a retinoic acid metabolism blocking agent of formula (I) or (II)

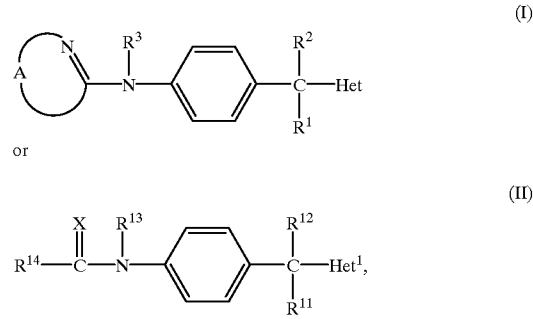

an N-oxide, a pharmaceutically acceptable addition salt or a stereochemically isomeric form thereof, wherein :

R$^1$ represents hydrogen, hydroxy, C$_{1-6}$alkyl or aryl;

R$^2$ represents hydrogen; C$_{1-12}$alkyl; C$_{3-7}$cycloalkyl; C$_{2-8}$alkenyl; aryl; pyrrolidinyl optionally substituted with C$_{1-4}$alkyl or C$_{1-4}$alkyloxycarbonyl; or C$_{1-12}$alkyl substituted with one or two substituents selected from C$_{3-7}$cycloalkyl, hydroxy, C$_{1-4}$alkyloxy, cyano, amino, mono- and di(C$_{1-4}$alkyl)amino, mono- and di(aryl)amino, arylC$_{1-4}$alkylamino, (C$_{1-4}$alkyl)(arylC$_{1-4}$alkyl)amino, pyrrolidinyl , piperidinyl, piperazinyl optionally substituted with C$_{1-4}$alkyl, morpholinyl, perhydro-azepinyl, carboxyl, C$_{1-4}$alkyloxycarbonyl, aminocarbonyl, mono- and di(C$_{1-4}$alkyl)aminocarbonyl, aryl, aryloxy and arylthio;

R$^3$ represents hydrogen, C$_{1-6}$alkyl, aryl or C$_{1-6}$alkyl substituted with aryl;

Het represents an unsaturated heterocycle selected from imidazolyl, triazolyl, tetrazolyl and pyridinyl; each of said unsaturated heterocycles may optionally be substituted with amino, mercapto, $C_{1-6}$alkyl, $C_{1-6}$alkylthio or aryl;

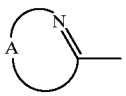

represents an unsaturated mono- or bicyclic heterocycle selected from the group consisting of pyridinyl, pyridazinyl, pyrimidinyl, pyrazinyl, quinolinyl, isoquinolinyl, purinyl, phtalazinyl, cinnolinyl, quinazolinyl and quinoxalinyl; each of said unsaturated mono- or bicyclic heterocycles may optionally be substituted with one, two or three substituents selected from hydroxy, halo, nitro, amino, $C_{1-6}$alkyl, hydroxy$C_{1-6}$alkyl, halo$C_{1-6}$alkyl, $C_{1-6}$alkyloxy, $C_{1-6}$alkylthio, formyl, carboxyl, mono- or di($C_{1-6}$alkyl)amino, $C_{1-6}$alkyloxycarbonyl or aryl; or

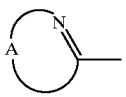

represents a radical of formula

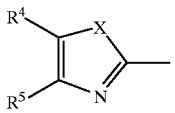 (a)

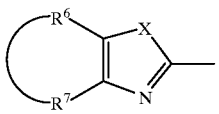 (b)

wherein:
each X independently represents $NR^8$, O, S, S(=O) or $S(=O)_2$;
wherein $R^8$ is hydrogen, $C_{1-6}$alkyl, aryl or aryl$C_{1-6}$alkyl;
$R^4$ and $R^5$ each independently represent hydrogen, hydroxy, halo, cyano, nitro, amino, $C_{1-6}$alkyl, hydroxy$C_{1-6}$alkyl, halo$C_{1-6}$alkyl, $C_{1-6}$alkyloxy, formyl, carboxyl, mono- or di($C_{1-6}$alkyl)amino, $C_{1-6}$alkyloxycarbonyl or aryl;
—$R^6$—$R^7$— represents a bivalent radical of formula —$CR^9$=$CR^9$—$CR^9$=$CR^9$— (b-1);
—N=$CR^9$—$CR^9$=$CR^9$— (b-2);
—$CR^9$=N—$CR^9$=$CR^9$— (b-3);
—$CR^9$=$CR^9$—N=$CR^9$— (b-4);
—$CR^9$=$CR^9$—$CR^9$=N— (b-5);
—$CR^9$=N—N=$CR^9$— (b-6);
—$CR^9$=N—$CR^9$=N— (b-7);
—$CR^9$=$CR^9$—N=N— (b-8);
—N=N—$CR^9$=$CR^9$— (b-9);
—N=$CR^9$—N=$CR^9$— (b-10);
—N=$CR^9$—$CR^9$=N— (b-11);

—$CR^9$=N—N=N— (b-12);
—N=$CR^9$—N=N— (b-13);
—N=N—$CR^9$=N— (b-14)

or

—N=N—N=$CR^9$— (b-15);

wherein each $R^9$ independently represents hydrogen, hydroxy, halo, nitro, amino, $C_{1-6}$alkyl, hydroxy$C_{1-6}$alkyl, halo$C_{1-6}$alkyl, $C_{1-6}$alkyloxy, formyl, carboxyl, mono- or di($C_{1-6}$alkyl)amino, $C_{1-6}$alkyloxycarbonyl or aryl; and
aryl represents phenyl or phenyl substituted with one, two or three substituents selected from hydroxy, halo, cyano, amino, mono- or di($C_{1-6}$alkyl)amino, $C_{1-6}$alkyl, halo$C_{1-6}$alkyl, hydroxy$C_{1-6}$alkyl, $C_{1-6}$alkyloxy, formyl, carboxyl and $C_{1-6}$alkylcarbonyl; or two adjacent carbon atoms on said phenyl may be substituted by a single bivalent radical having the formula $C_{1-12}$alkanediyl or halo$C_{1-12}$alkanediyl;
X represents O, S or $NR^{13}$;
$R^{11}$ represents hydrogen, hydroxy, $C_{1-6}$alkyl or aryl$^1$;
$R^{12}$ represents hydrogen; $C_{1-12}$alkyl; $C_{3-7}$cycloalkyl; $C_{2-8}$alkenyl; aryl$^1$; Het$^2$; or $C_{1-12}$alkyl substituted with one or two substituents selected from $C_{3-7}$cycloalkyl, hydroxy, $C_{1-4}$alkyloxy, cyano, amino, mono- and di($C_{1-4}$alkyl)amino, mono- or di(aryl$^1$$C_{1-4}$alkyl)amino, di(aryl$^1$$C_{1-4}$alkyl) aminocarbonyloxy, ($C_{1-4}$alkyl) (aryl$^1$$C_{1-4}$alkyl)amino, mono- and di(aryl$^1$)amino, ($C_{1-4}$alkyl)(di($C_{1-4}$alkyl)amino$C_{1-4}$alkyl)amino, pyrrolidinyl, piperidinyl, piperazinyl optionally substituted with $C_{1-4}$alkyl, morpholinyl, perhydro-azepinyl, carboxyl, $C_{1-4}$alkyloxycarbonyl, aminocarbonyl, mono- and di($C_{1-4}$alkyl)aminocarbonyl, aryl$^1$, aryl$^1$oxy and aryl$^1$thio; or $R^{11}$ and $R^{12}$ taken together may form a bivalent radical of formula —$R^{11}$—$R^{12}$— wherein —$R^1$—$R^{12}$— represents—$(CH_2)_n$—wherein n is 2, 3, 4, 5 or 6;
$R^{13}$ represents hydrogen, $C_{1-6}$alkyl, aryl$^1$, Het$^2$ or $C_{1-6}$alkyl substituted with aryl$^1$ or Het$^2$;
$R^{14}$ represents hydrogen; hydroxy; mercapto; $C_{1-6}$alkyloxy; $C_{1-6}$alkylthio; aryl$^{11}$oxy; aryl$^1$thio; Het -oxy; Het$^2$-thio; $C_{1-12}$alkyl optionally substituted with one, two or three substituents each independently selected from halo, hydroxy, mercapto, $C_{1-6}$alkyloxy, $C_{1-6}$alkylthio, aryl$^1$oxy, aryl$^1$thio, Het$^2$-oxy, Het$^2$-thio, $C_{3-7}$cycloalkyl optionally substituted with hydroxycarbonyl$C_{1-6}$alkyl, carboxyl, $C_{1-6}$alkyloxycarbonyl, aryl$^1$$C_{1-6}$alkyloxy, aryl$^1$$C_{1-6}$alkylthio, aryl$^1$, Het$^2$; $C_{2-8}$alkenyl optionally substituted with one, two or three substituents selected from halo, $C_{3-7}$cycloalkyl, aryl$^1$, Het$^2$; $C_{2-8}$alkynyl optionally substituted with halo, $C_{3-7}$cycloalkyl, aryl$^1$; C3–7cycloalkyl optionally substituted with $C_{1}$alkyl or aryl$^1$; $C_{5-7}$cycloalkenyl optionally substituted with $C_{1-6}$alkyl or aryl$^1$; aryl$^1$; Het$^2$; or —Alk—$NR^{13}R^{15}$ (i)

or

—$NR^{13}R^{15}$ (ii)

wherein Alk represents $C_{1-6}$alkanediyl; and
$R^{15}$ represents hydrogen, $C_{1-6}$alkyl, aryl$^1$, Het$^2$$_1$ (aryl$^1$ or Het$^2$)$C_{1-6}$alkyl, (aryl$^1$ or Het$^2$)carbonyl or (aryl$^1$ or Het$^2$) $C_{1-6}$alkyloxycarbonyl;
aryl$^1$represents indanyl, indenyl, naphtyl, 5,6,7,8-tetrahydro-2-naphtalenyl, phenyl; said indanyl, indenyl, naphtyl or phenyl may be substituted with one, two, three, four or five substituents each independently selected from hydroxy, halo, nitro, cyano, amino, azido, mono- or di($C_{1-6}$alkyl)-amino, $C_{1-6}$alkylcarbonylamino, $C_{1-6}$alkyl, polyhalo$C_{1-6}$alkyl, hydroxy$C_{1-6}$alkyl, phenyl, phenyloxy, phenyl$C_{1-6}$alkyloxy, pyridinyl$C_1$6alkyloxy, $C_{1-6}$alkyloxy, formyl, carboxyl and $C_{1-6}$alkylcarbonyl; or two adjacent carbon atoms on said phenyl may be substituted by a single bivalent radical having the formula $C_{1-12}$alkanediyl or polyhalo$C_{1-12}$alkanediyl;

$Het^1$ represents an unsaturated heterocycle selected from pyrrolyl, pyrazolyl, imidazolyl, triazolyl, tetrazolyl and pyridinyl; each of said unsaturated heterocycles may optionally be substituted with amino, mercapto, $C_{1-6}$alkyl, $C_{1-6}$alkylthio or aryl; and Het2 represents a monocyclic heterocycle selected from pyrrolidinyl, pyrrolyl, pyrazolyl, imidazolyl, 1,3,4-triazolyl, 1,2,4-triazolyl, tetrahydrofuranyl, furanyl, thiolanyl, thienyl, dioxolanyl, isoxazolyl, oxazolyl, isothiazolyl, thiazolyl, isoxazolidinyl, oxazolidinyl, isothiazolidinyl, thiazolidinyl, piperidinyl, pyridinyl, piperazinyl, pyridazinyl, pyrimidinyl, pyrazinyl, 1,2,3triazinyl, 1,2,4-triazinyl, tetrahydropyranyl, pyranyl, morpholinyl and dioxanyl; each of said monocyclic heterocycles may be optionally substituted with one or two substituents each independently selected from $C_{1-4}$alkyl, hydroxy, amino, halo, aryl, arylcarbonyl or $C_{1-4}$alkyloxycarbonyl; or a bicyclic heterocycle selected from indolinyl, indolyl, indazolyl, benzimidazolyl, benzotriazolyl, benzofuranyl, benzothienyl, 2H-1-benzopyranyl, 3,4-dihydro-2H-1-benzopyranyl, benzthiazolyl, isoguinolinyl, quinolinyl, 3,4-dihydroquinolinyl, cinnolinyl, quinazolinyl, quinoxalinyl, chromanyl, 1,4-benzodioxinyl, 1,4-benzoxathianyl, benzodioxanyl and benzodioxolanyl; each of said bicyclic heterocycles may be substituted with one or two substituents each independently selected from $C_{1-4}$alkyl, hydroxy, amino, halo, aryl, arylcarbonyl or $C_{1-4}$alkyloxycarbonyl; comprising administering to an animal in need thereof a tocopherol or a prodrug thereof.

8. The method as claimed in claim 1 wherein the tocopherol is vitamin E.

9. The method as claimed in claim 8 wherein the retinoic acid metabolism blocking agent is
N-[4-[2-ethyl-1-(1 H-imidazol-1-yl)butyl]phenyl]-2-benzothiazolamine;
N-[4-[2-ethyl-1-(1H-1,2,4-triazol-1-yl)butyl]phenyl]-2-benzoxazolamine;
N-[4-[2-ethyl-1-(1H-1,2,4-triazol-1-yl)butyl]phenyl]-2-benzothiazolamine;
N-[4-[2-(dimethylamino)-1-(1H-imidazol-1-yl)propyl]phenyl]-2-benzothiazol-amine;
N-[4-[2-(dimethylamino)-1-(1H-1,2,4-triazol-1-yl)propyl]phenyl]-2-benzo-thiazolamine;
N-[4-[2-ethyl-1-(1H-imidazol-1-yl)butyl]phenyl]-2-benzoxazolamine;
N-[4-[2-ethyl-1-(1H-imidazol-1-yl)butyl]phenyl]-6-methoxy-2-benzothiazolamine;
N-[4-[2-(dimethylamino)-1-(1H-imidazol-1-yl)-2-methylpropyl]phenyl]-2-benzothiazolamine;
N-[4-[2-(dimethylamino)-2-methyl-1-(1H-1,2,4-triazol-1-yl)propyl]phenyl]-2-benzothiazolamine;
N-[4-[cyclohexyl(1H-imidazol-1-yl)methyl]phenyl]-2-benzothiazolamine;
N-[4-[cyclohexyl(1H-1,2,4-triazol-1-yl)methyl]phenyl]-2-benzothiazolamine; an N-oxide, a pharmaceutically acceptable addition salt or a stereochemically isomeric form thereof.

10. The method as claimed in claim 1 wherein the therapy is the treatment of cancer.

11. The method as claimed in claim 1 wherein the therapy is the treatment of psoriasis.

\* \* \* \* \*